US008663821B2

(12) United States Patent
Baranoff et al.

(10) Patent No.: US 8,663,821 B2
(45) Date of Patent: Mar. 4, 2014

(54) LIGHT-EMITTING MATERIAL COMPRISING MULTINUCLEAR COMPLEXES

(75) Inventors: Etienne David Baranoff, Renens VD (CH); Mohammad Khaja Nazeeruddin, Ecublens (CH); Michael Graetzel, Saint Sulpice (CH)

(73) Assignee: Solvay SA, Brussels (BE)

( * ) Notice: Subject to any disclaimer, the term of this patent is extended or adjusted under 35 U.S.C. 154(b) by 464 days.

(21) Appl. No.: 13/054,429

(22) PCT Filed: Jul. 15, 2009

(86) PCT No.: PCT/EP2009/059074
§ 371 (c)(1),
(2), (4) Date: Jan. 14, 2011

(87) PCT Pub. No.: WO2010/007098
PCT Pub. Date: Jan. 21, 2010

(65) Prior Publication Data
US 2011/0121279 A1    May 26, 2011

(30) Foreign Application Priority Data

Jul. 16, 2008  (EP) .................... 08160492

(51) Int. Cl.
*H01L 51/54* (2006.01)
*C09K 11/06* (2006.01)

(52) U.S. Cl.
USPC ........... 428/690; 428/917; 313/504; 313/506; 252/301.16; 257/40; 257/E51.044; 548/103; 548/108; 546/4

(58) Field of Classification Search
None
See application file for complete search history.

(56) References Cited

U.S. PATENT DOCUMENTS

| 6,670,645 | B2 | 12/2003 | Grushin et al. | |
| 2004/0197600 | A1* | 10/2004 | Thompson et al. | 428/690 |
| 2005/0031903 | A1 | 2/2005 | Park et al. | |
| 2005/0142381 | A1 | 6/2005 | Lyu et al. | |
| 2005/0260441 | A1 | 11/2005 | Thompson et al. | |
| 2006/0099446 | A1* | 5/2006 | Byun et al. | 428/690 |
| 2007/0087221 | A1 | 4/2007 | Wu et al. | |
| 2007/0270592 | A1 | 11/2007 | Ragini et al. | |
| 2008/0043815 | A1 | 2/2008 | Hart et al. | |
| 2008/0058498 | A1 | 3/2008 | Tsuboyama et al. | |
| 2009/0171087 | A1* | 7/2009 | Chi et al. | 546/2 |
| 2010/0213824 | A1* | 8/2010 | Adler et al. | 313/504 |

FOREIGN PATENT DOCUMENTS

| EP | 1538153 | A1 | 6/2005 | |
| JP | 20030113163 | A | 4/2003 | |
| JP | 20030113164 | A | 4/2003 | |
| JP | 20060316162 | A | 11/2006 | |
| WO | WO 20040043974 | A1 | 5/2004 | |
| WO | WO 20070042474 | A2 | 10/2006 | |
| WO | WO 20070115972 | A1 | 4/2007 | |
| WO | WO 20070078183 | A1 | 7/2007 | |
| WO | WO 20080043815 | A1 | 10/2007 | |
| WO | WO 20080148829 | A1 | 6/2008 | |
| WO | WO 2008/141637 | A2 * | 11/2008 | ............. C09K 11/06 |
| WO | WO 20080148830 | A1 | 6/2009 | |

OTHER PUBLICATIONS

Adams et al. "Cyanide-bridged linkage isomers with catecholateruthenium(II) centers bound to Mn(I) or M(alkyne) units." Dalton Trans. 2007. pp. 1904-1910.*
U.S. Appl. No. 12/089,303, Sung Ho Jin, et al., filed Aug. 18, 2008.
U.S. Appl. No. 12/295,933, Mohammad Khaja Nazeeruddin, et al., filed Oct. 3, 2008.
U.S. Appl. No. 12/444,793, Mohammad Khaja Nazeeruddin, et al., filed Apr. 8, 2009.
U.S. Appl. No. 12/602,811, Mohammad Khaja Nazeeruddin, et al., filed Dec. 3, 2009.
U.S. Appl. No. 12/602,815, Mohammad Khaja Nazeeruddin, et al., filed Dec. 3, 2009.
Plummer, Edward A., et al—"Mono- and di-nuclear irindium(III) complexes. Synthesis and photophysics", Dalton Trans. , The Royal Society of Chemistry, 2003, pp. 2080-2084; 5 pgs.
Tsuboyama, Akira, et al—"A novel dinuclear cyclometalated iridium complex bridged with 1,4-bis[pyridine-2-yl]benzene: its structure and photophysical properties", Dalyon Trans. , The Royal Society of Chemistry, 2004, pp. 1115-1116; 2 pgs.
Yang, Liangru, et al—"Novel HEXOL-type cyclometallated irindium(III) complexes: stereoselective synthesis and structure elucidation", Chem. Commun., 2005, pp. 4155-4157; 3 pgs.
Dedeian, K., et al—"A New Synthetic Route to the Preparation of a Series of Strong Photoreducing Agents: fac Tris-Ortho-Metalated Complexes of Irindium(III) with Substituted 2-Phenylpyridines", Inorganic Chemistry, vol. 30, No. 8, American Chemical Society, 1991, pp. 1685-1687; 3 pgs.
Garces, F.O, et al—"Synthesis, Structure, Electrochemistry, and Photophysics of Methyl-Substituted Phenylpyridine Ortho-Metalated Irindium(III) Complexes", Inorganic Chemistry, vol. 27, No. 20, 1988, pp. 3464-3471; 8 pgs.

(Continued)

*Primary Examiner* — Michael H Wilson
(74) *Attorney, Agent, or Firm* — Foley & Lardner LLP

(57) ABSTRACT

Light emitting materials comprising multinuclear metal complexes comprising at least two metal atoms and a metal bridging ligand bound to said at least two metal atoms. It relates more particularly to a multinuclear complex of Formula (I): {-[L]2M-B-}n, wherein L is a bidentate ligand; M represents a transition metal having an atomic number of at least 40, and each M can be the same or different at each occurrence; B is a 2-connecting short metal bridging ligand bound to said at least two metal atoms, where the metal bridging ligand comprises coordinating atoms independently selected from the group consisting of nitrogen, phosphorous, carbon, oxygen, sulphur and selenium in 1,2 or 1,3 mutual position. (1,2-μ or 1,3-μ bonding mode); and n is an integer larger than 1.

19 Claims, 5 Drawing Sheets

(56) References Cited

OTHER PUBLICATIONS

Colombo, Mirco G., et al—"Facial Tris Cyclometalated rhodium(3+) and iridium(3+) Complexes: Their Synthesis, Structure, and Optical Specroscopic Properties", Inorg. Chem. 1984, vol. 33, pp. 545-550; 6 pgs.

Van Diemen, J. H., et al—"Synthesis, X-ray structure, electrochemical and electronic properties of [3-(pyridin-2yl)-4-methyl-1,2,4-triazole-bis(2-(2'-phenylato)pyridine)-iridium(III)] hexafluorophosphate", Inorganica Chimica Acta, vol. 181, Issue 2, 1991, pp. 245-251; 7 pgs.

King, K.A., et al—"Excited-State Properties of a Triply Ortho-Metalated Irindium(III) Complex", J. Am. Chem. Soc., 1985, vol. 107, pp. 1431-1432; 2 pgs.

Lohse, Oliver, et al—"The Palladium-Catalysed Suzuki Coupling of 2- and 4-Chloropyridines" Synlett 1999, No. 1, pp. 45-48; 4 pgs.

Nazeeruddin, Md K., et al—"Highly Phosphorescence Iridium Complexes and Their Application in Organic Light-Emitting Devices", J. Am. Chem. Soc., 2003, vol. 125 (29), pp. 8790-8797; 8 pgs.

King, K.A., et al—"Dual Emission from an Ortho-Metalated irindium(III) Complex", J. Am. Chem. Soc., 1987, 109 (5), pp. 1589-1590; 2 pgs.

Amadelli, R. et al. "Design of Antenna-Sensitizer Polynuclear Complexes. Sensitization of Titanium Dioxide with $[Ru(bpy)_2(CN)_2]_2Ru(bpy(COO)_2)_2{}^{2-}$", J. Am. Chem. Soc., 1990, vol. 112, pp. 7099-7103.

Bignozzi, C. A. et al. "Photoinduced intramolecular energy transfer processes in polynuclear ruthenim(II) polypyridine complexes. Design of long chain cyanobridge polynuclear species featuring vectorial energy transfer", Coordination Chemistry Reviews, 1991, vol. 111, pp. 261-266.

Jain, V. K. et al. "The chemistry of binuclear palladium(II) and platinum(II) complexes", Coordnation Chemistry Reviews, 2005, vol. 249, pp. 3075-3197.

Journal of Tianjin University of Commerce, Nov. 2004, vol. 24, No. 6, pp. 4-6.

\* cited by examiner

ND COMPLEXES

LIGHT-EMITTING MATERIAL COMPRISING MULTINUCLEAR COMPLEXES

CROSS-REFERENCE TO RELATED APPLICATIONS

This application is a U.S. national stage application under 35 U.S.C. §371 of International Application No. PCT/EP2009/059074 filed Jul. 15, 2009, which claims priority to European Application No. 08160492.8 filed Jul. 16, 2008, this application being herein incorporated by reference in its entirety for all purposes.

TECHNICAL FIELD

The present invention relates to a light-emitting material and the use of such material. The present invention further relates to a light-emitting device capable of converting electric energy to light.

BACKGROUND

Currently, various display devices are actively being researched and developed, particularly those based on electroluminescence (EL) from organic materials. Contrary to photoluminescence (i.e., light emission from an active material due to optical absorption and relaxation by radioactive decay of an excited state), EL refers to a non-thermal generation of light resulting from applying an electric field to a substrate. In the case of EL, excitation is accomplished by recombining the charge carriers of opposite signs (electrons and holes) injected into an organic semiconductor in the presence of an external circuit.

A simple prototype of an organic light-emitting diode (OLED), i.e., a single layer OLED, is typically composed of a thin film made from an active organic material, which is sandwiched between two electrodes. One electrode needs to be semitransparent in order to observe the light emission from the organic layer. Typically, an indium tin oxide (ITO)-coated glass substrate is used as an anode.

Many organic materials exhibit fluorescence, i.e., luminescence from a symmetry-allowed process, from singlet excitons, which may be efficient since this process occurs between states of the same symmetry. On the contrary, if the symmetry of an exciton is different from the one of the ground state, then the radioactive relaxation of the exciton is disallowed and the luminescence will be slow and inefficient. Since the ground state is usually anti-symmetric, the decay from a triplet breaks the symmetry. Thus, the process is disallowed and the efficiency of EL is very low. Therefore, the energy contained in the triplet states is mostly wasted.

Luminescence from a symmetry-disallowed process is known as phosphorescence. Typically, phosphorescence may last up to several seconds after excitation due to the low probability of the transition, which is different from fluorescence that originates in a rapid decay. However, only a few organic materials have been identified that show efficient room temperature phosphorescence from triplets.

If phosphorescent materials are successfully utilized, they hold enormous promises and benefits for organic electroluminescent devices. For example, the advantage of utilizing phosphorescent materials is that all excitons (formed by combining holes and electrons in an EL), which are, in part, triplet-based in phosphorescent devices, may participate in the energy transfer and luminescence. This can be achieved by phosphorescence emission itself or, alternatively, it can be accomplished by using phosphorescent materials to improve the efficiency of the fluorescence process as a phosphorescent host or a dopant in a fluorescent guest, with phosphorescence from a triplet state of the host enabling energy transfer from a triplet state of the host to a singlet state of the guest.

Iridium(III) complexes have recently attracted a lot of interest as potential triplet emitters in electronic devices and in biological applications as luminescent and electrochemiluminescent materials. Colors ranging from bluish green to red are generated by varying the ligands in the iridium complexes. However, iridium complexes having only one iridium atom have emitted light at a very narrow spectral region and, thus, are not suitable for white light emission, e.g., for replacing incandescent bulbs. If each light-emitting diode (LED) emits only at a narrow spectral region, a white light display would require multiple LEDs, and the multiple LEDs would then be incorporated into complicated and expensive LED modules to obtain the required broad band illumination necessary for providing white light. In this regard, there have been several studies on the development of iridium complexes having at least two iridium atoms.

Plummer et al., "Mono- and Di-nuclear Iridium(III) Complexes: Synthesis and Photophysics," *Dalton Trans.*, 2080-2084 (2003) discloses heteroleptic mono- and di-nuclear iridium(III) complexes containing two ortho-metalating ligands, 2-phenylpyridine with a bipyridine derivative. The iridium(III) complexes emit light in the range from a green region to a red region, as represented by the following formula:

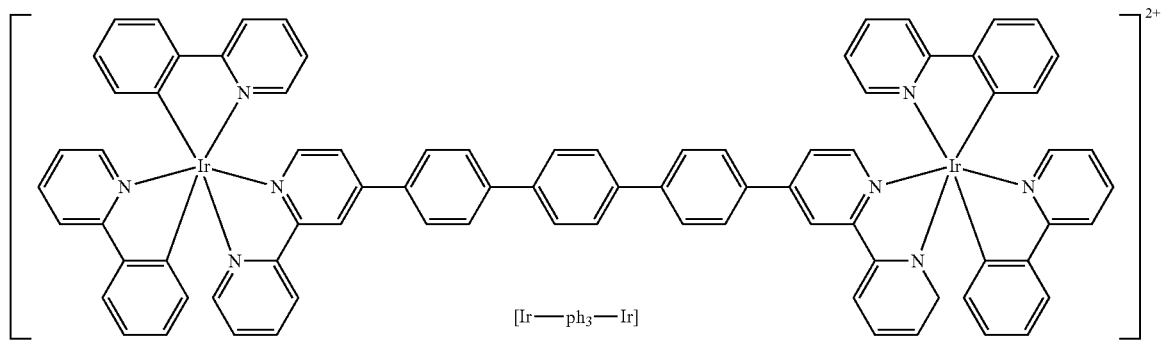

Tsuboyama et al., "A Novel Dinuclear Cyclometalated Iridium Complex Bridged with 1,4-bis[pyridine-2-yl]benzene: Its Structure and Photophysical Properties," *Dalton Trans.*, 1115-1116 (2004) discloses a dinuclear iridium complex, which exhibits intense red phosphorescence in solutions, as represented by the following formula:

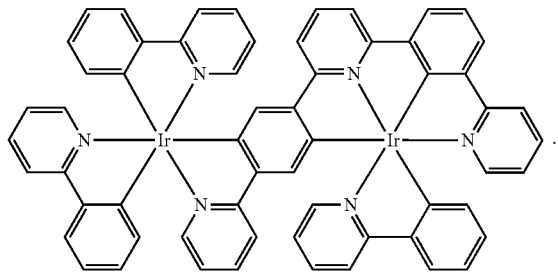

L. Yang., "Novel HEXOL-Type Cyclometallated Iridium (III) Complexes: Stereoselective Synthesis and Structure Elucidation," *Chem. Commun.*, 4155-4157 (2005) discloses the preparation of two diastereoisomers of tetranuclear cyclometallated iridium complexes, either having an inner core of HEXOL-type [Ir(IrCl2)3]6+ unit and a surface of six chiral, didentate, cyclometallated ligands from an enantiopure pinenopyridine derivative.

PCT International Publication No. WO 2004/043974 relates to a process for producing a trivalent hexadentate ortho-metallated iridium complex characterized in a monovalent iridium dinuclear complex having halogens as bridging ligands.

However, the above light-emitting materials containing iridium complexes disclosed in the art do not exhibit sufficiently high efficiency as well as broad emission to obtain white light. It would thus be desirable to develop light-emitting materials capable of effectively emitting light of a broad spectral range, especially in the orange, green, and blue regions.

DETAILED DESCRIPTION OF THE INVENTION

Figure 1:
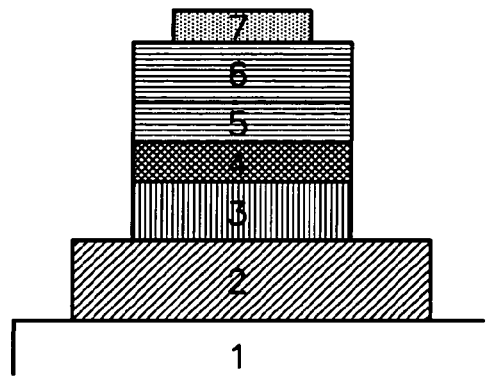
FIG. 1 is a cross-sectional view of a display device containing the organic light emitting device of the present invention.

The present invention relates to a light emitting material capable of emitting light of a broad spectral range efficient for white light emission, as described below.

Another aspect of the present invention relates to the use of said light emitting material and an organic light emitting device comprising said light emitting material.

The present invention provides a light emitting material comprising a multinuclear complex comprising at least two metal atoms, and a 2-connecting short metal bridging ligand bound to said at least two metal atoms, where the metal bridging ligand comprises coordinating atoms independently selected from nitrogen, phosphor, carbon, oxygen, sulphur and selenium in 1,2 or 1,3 mutual position.(1,2-µ or 1,3-µ bonding mode).

According to the invention, "2-connecting" means that the ligand connects to the metal atoms through 2 different atoms thereof, which may be vicinal (next to each other, which corresponds to 1,2-µ) or separated by one other atom (which corresponds to 1,3-µ).

More specifically, the multinuclear complex of the present invention can be represented by Formula (I): $\{-[L]_2M\text{-}B\text{-}\}_n$
wherein
L is a bidentate ligand
M represents a transition metal having an atomic number of at least 40, specifically of groups 8 to 12, more specifically Ir or Pt, most specifically Ir, each M can be the same or different at each occurrence;
B is as defined above; and n is an integer larger than 1.

In one, preferred embodiment, each B, which may be the same or different, is independently selected from short-bridging "pseudo-halide" ligands, preferably:
CN$^-$ (cyano)
Short nitriles, such as dca (dicyanamide) and tcm (tricyanomethanide)
NCX$^-$, where X=O (iso-cyantes), or S (iso-thiocyanates), or Se (iso-selenocyanates)
N$_3^-$ (azides)
R—CO$_2^-$ (carboxylates)
—NO.
Preferably, L represents

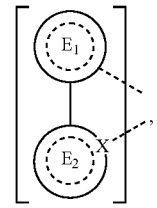

wherein $E_1$ represents an aromatic or heteroaromatic ring, optionally condensed with additional aromatic moieties or non aromatic cycles, said ring optionally having one or more substituents and coordinating to metal M via a sp² hybridized carbon, optionally forming a condensed structure with a ring $E_2$;

$E_2$ represents an aromatic or hetero-aromatic ring, optionally condensed with additional aromatic moieties or non aromatic cycles, said ring optionally having one or more substituents and coordinating to metal M via an atom X selected from groups IVa, Va or VIa of the periodic system, preferably sp² hybridized carbon or nitrogen. L prefereably is a bidentate CAN or CAC ligand.

The multinuclear complexes of formula (I) may be linear polymeric or oligomeric, more preferably oligo-nuclear metallic macrocycles. Most preferred are di-, tri- and tetra-nuclear cyclic complexes which are readily formed under appropriate conditions as discrete compounds through self-assembly. Tetra-nuclear cyclic complexes show intra-molecular interaction between CAN ligands, giving rise to stabilization and an overall rigidification of the molecule. It is believed that these effects lead to the observed unique photo-physical properties and increased lifetime.

In one embodiment of the present invention, the multi-nuclear complex has the following formula:

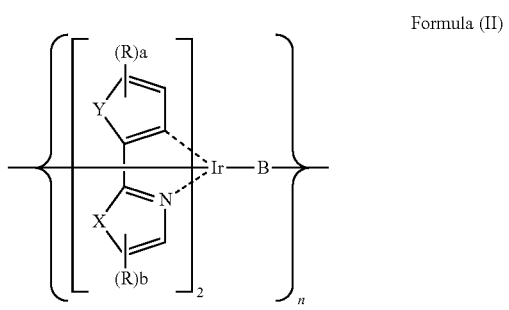

Formula (II)

wherein:
B and n are as defined above for Formula (I);
X is selected from the group consisting of —CH═CH—, —CR═CH—, —CR═CR—, N—H, N—R¹, O, S, and Se; specifically X is a group selected among —CH═CH—, —CR═CH— or S; most specifically X is —CH═CH—;
Y is selected from the group consisting of —CH═CH—, —CR═CH—, —CR═CR—, N—H, N—R¹, O, S, and Se; specifically Y is a group selected among —CH═CH—, —CR═CH— or S; most specifically Y is —CH═CH—;
R is the same or different at each occurrence and is —F, —Cl, —Br, —NO₂, —CN; a straight-chain or branched or cyclic alkyl or alkoxy group or dialkylamino group having from 1 to 20 carbon atoms, in each of which one or more nonadjacent —CH₂— groups may be replaced by —O—, —S—, —NR¹—, or —CONR²—, and in each of which one or more hydrogen atoms may be replaced by F, —COOR³, an aryl or heteroaryl group having from 4 to 14 carbon atoms which may be substituted by one or more non aromatic radicals; where a plurality of R, either on the same ring or on the two different rings, may in turn together form a mono- or polycyclic ring, optionally aromatic; where R¹, R² and R³ are the same or different at each occurrence and are each H or an aliphatic or aromatic hydrocarbon radical having from 1 to 20 carbon atoms;
a is an integer from 0 to 4; and
b is an integer from 0 to 4.

In another embodiment of the present invention, the multi-nuclear complex has the following formula:

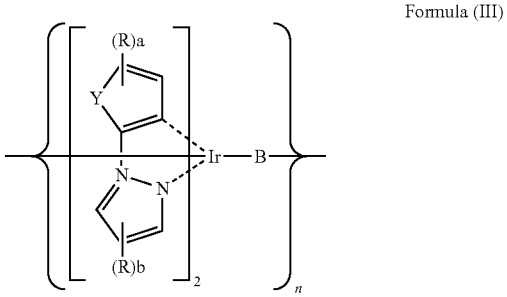

Formula (III)

wherein:
R, Y, B, a, and n are as defined above for Formlae (I) and (II); and b is an integer from 0 to 3.

In another embodiment of the present invention, the multi-nuclear complex has the following formula:

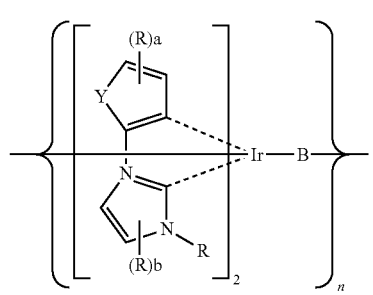

Formula (IV)

wherein:
R, Y, B, a, and n are as defined above for Formulae (I) to (III); and b is an integer from 0 to 2.

In another embodiment of the present invention, the multi-nuclear complex has the following formula:

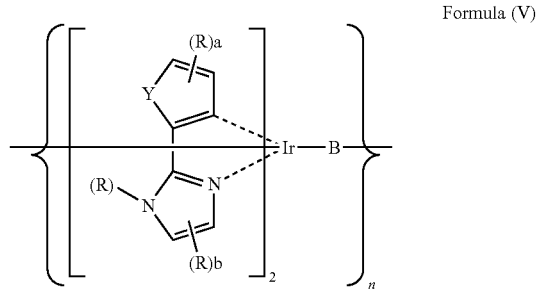

Formula (V)

wherein:
R, Y, B, a, b and n are as defined above for Formula (IV).

Other embodiments of the present invention relate to multi-nuclear complexes wherein each B, which may be the same or different, is selected from cyano and thiocyanate ligands (preferably cyano ligands) and n is specifically 4, i.e., tetra-nuclear complexes.

Specifically, other embodiments of the multinuclear complexes of the present invention include the following complexes represented by Formulae (III) and (V) having bluish green to deep blue emission:
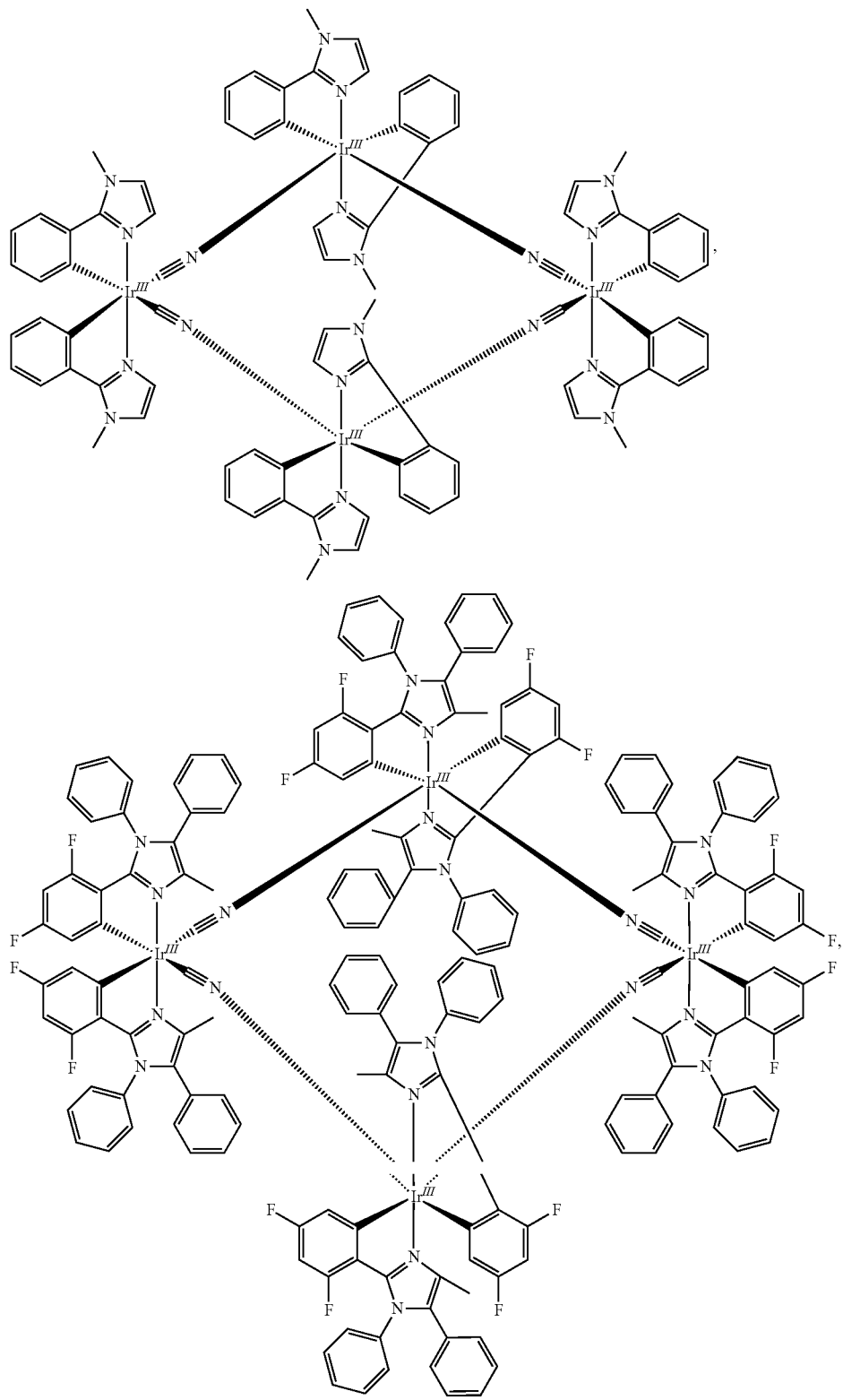

-continued
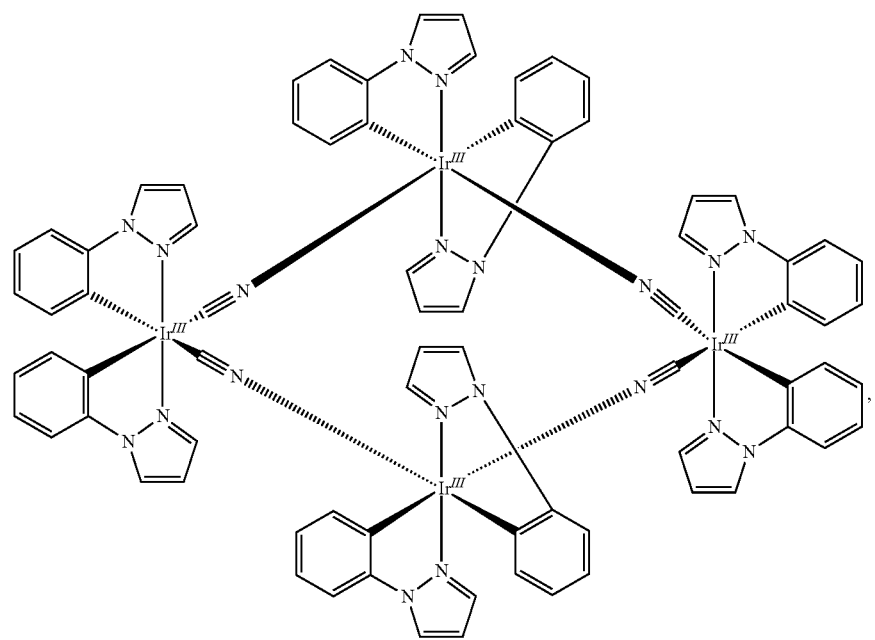
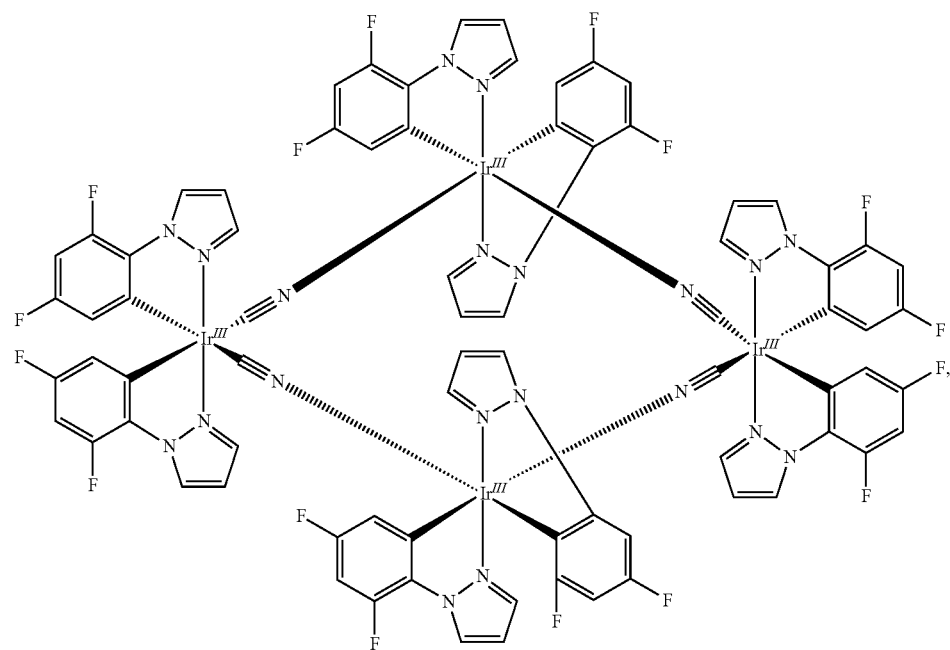

-continued
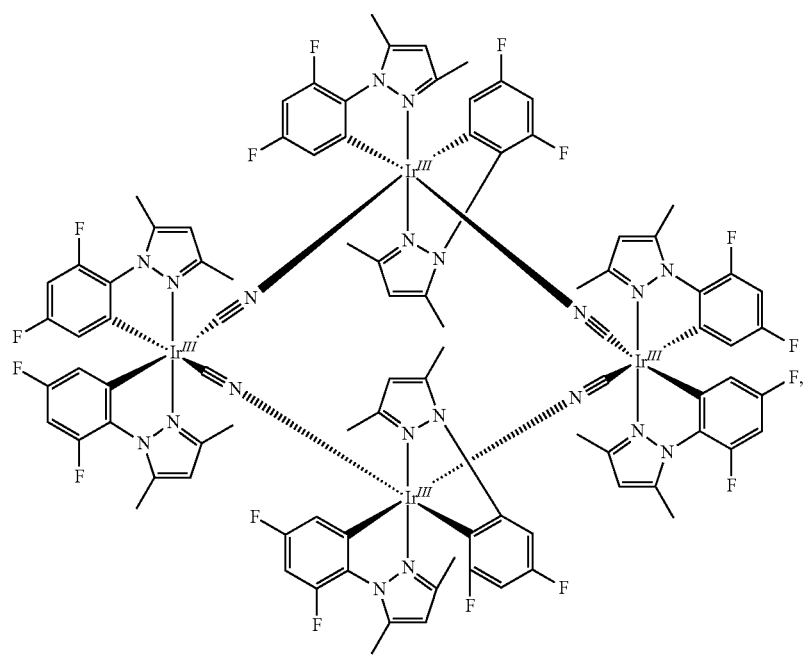
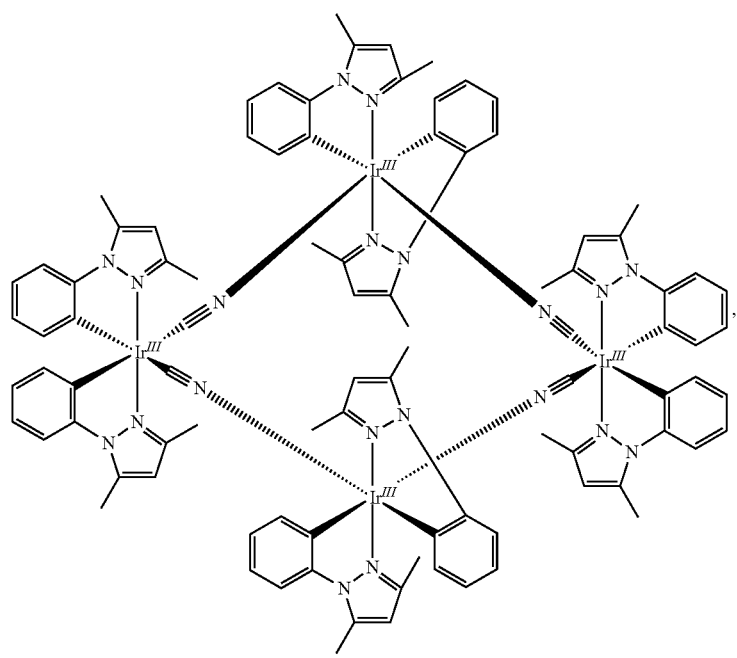
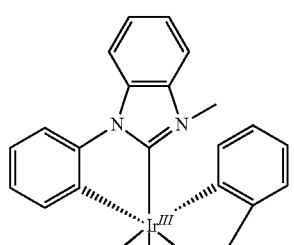

-continued
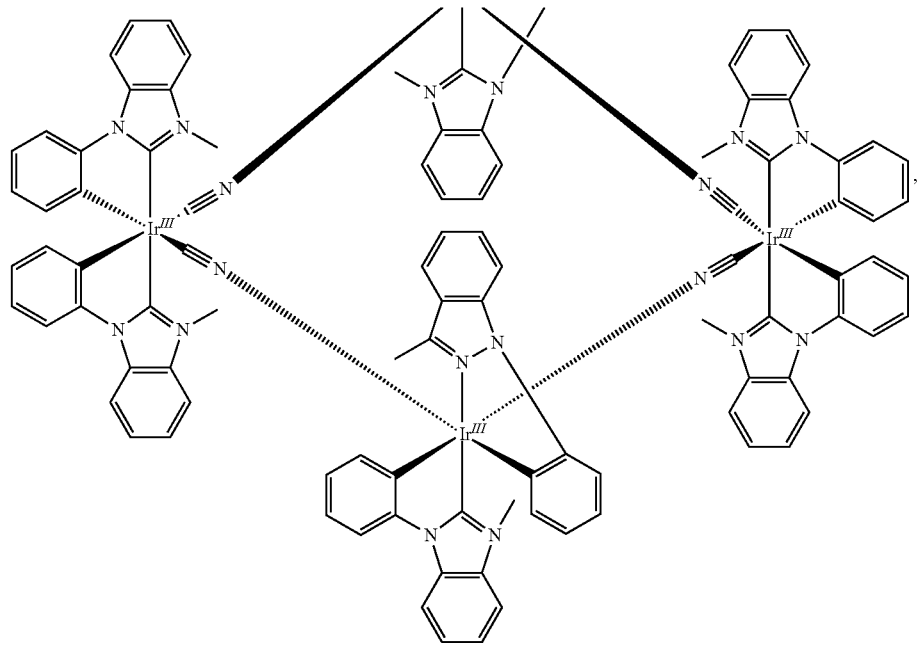
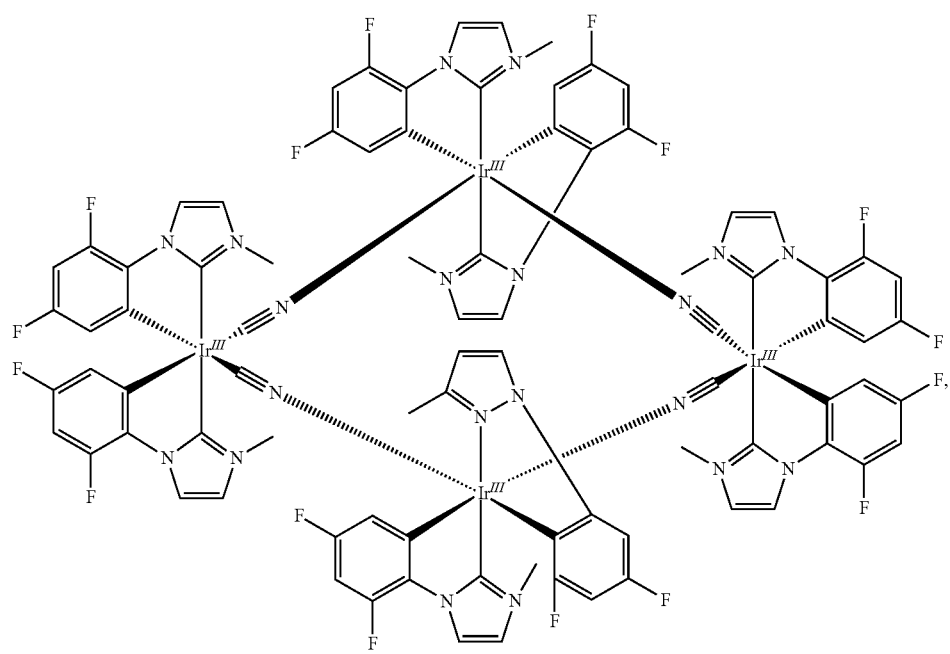
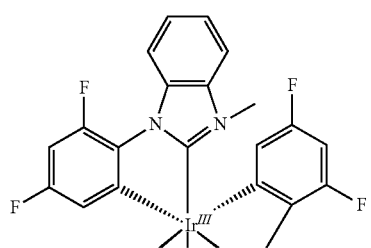

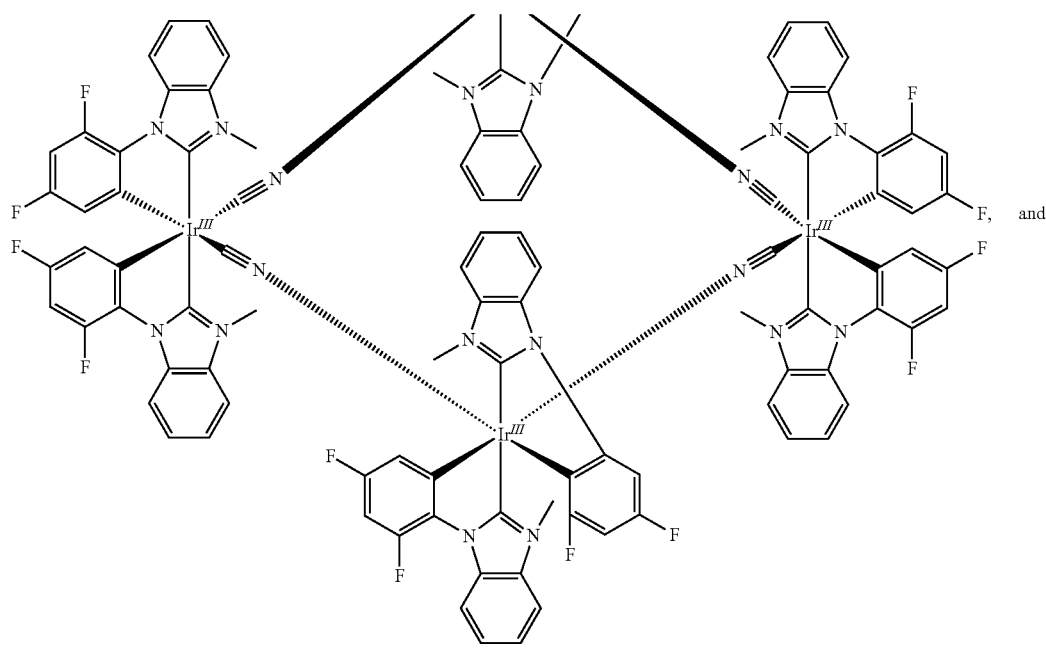

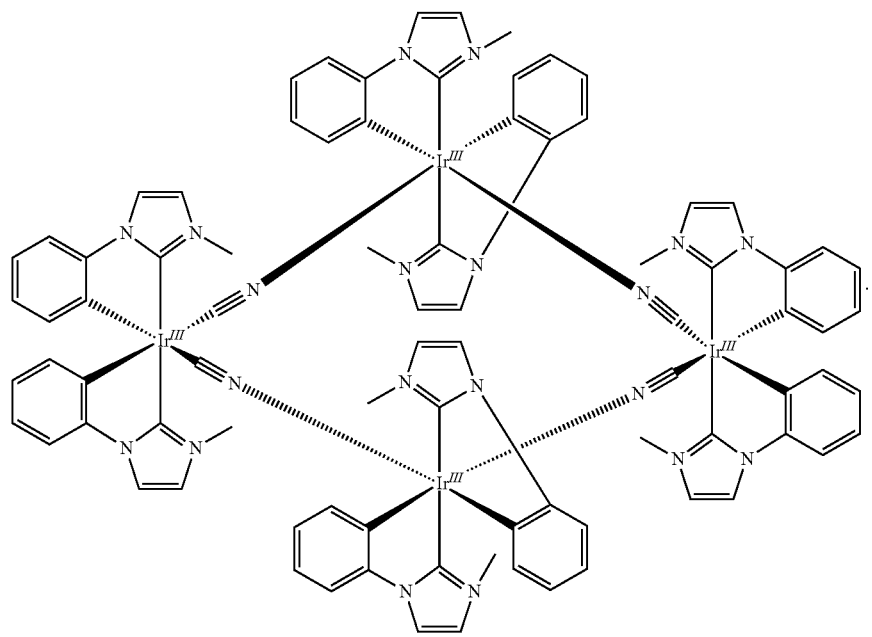

It has been found that when a complex having at least two metals which bind both orthometallated ligands comprising $E_1$ and $B_2$ moieties and a bridged ligand, those metals faun a rigid structure in which the metal atoms are caged by the orthometallated ligands, thereby significantly broadening the emission in the visible region and simultaneously, enhancing the emission intensity of the solid state compared to the corresponding mononuclear complexes. It has also been found that cyclic structures as described above (where the at least two metals and their bridging ligands form a cycle) are very stable.

Further embodiments of the multinuclear complexes of the present invention include the following complexes represented by Formulae (VI) to (XII):

Formula (VI)
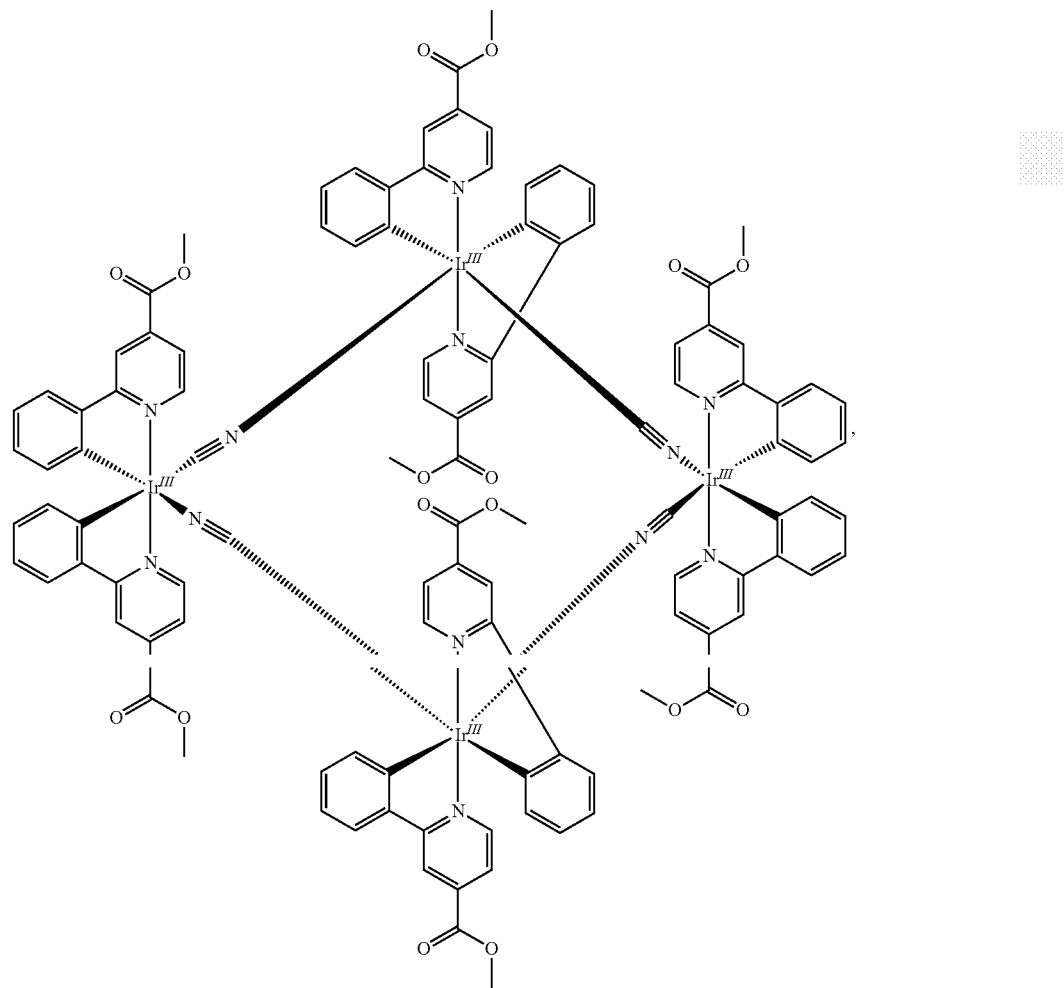
Formula (VII)
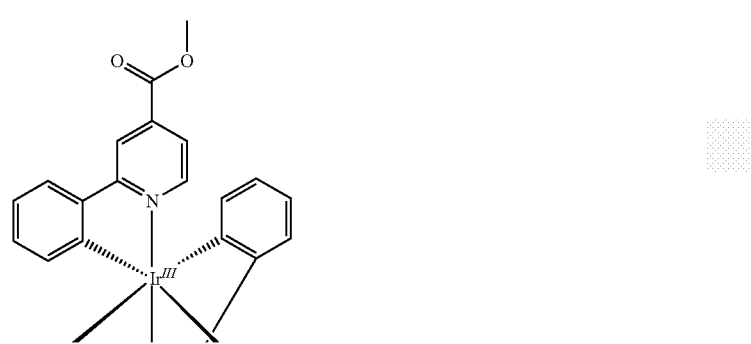

-continued
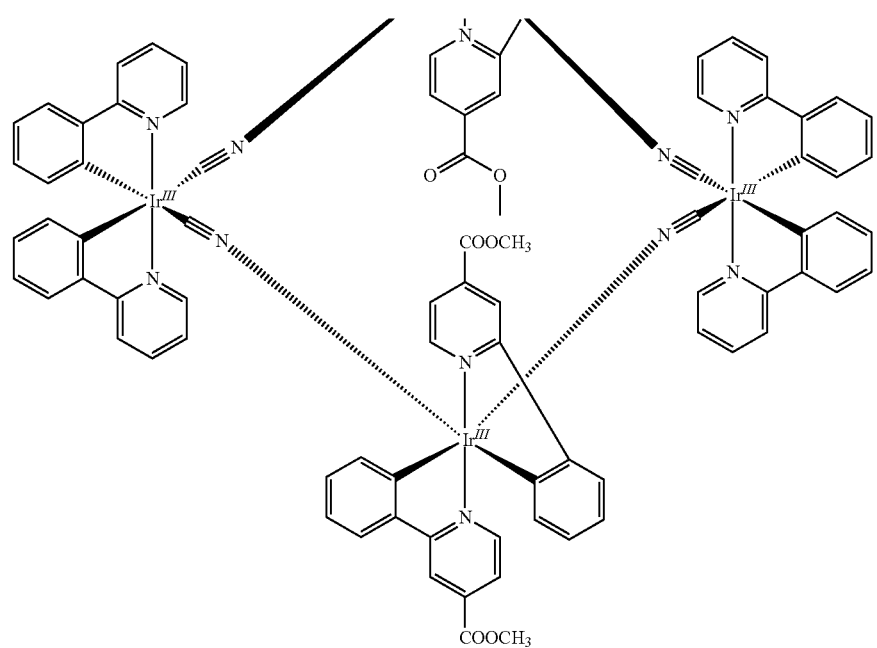
Formula (VIII)
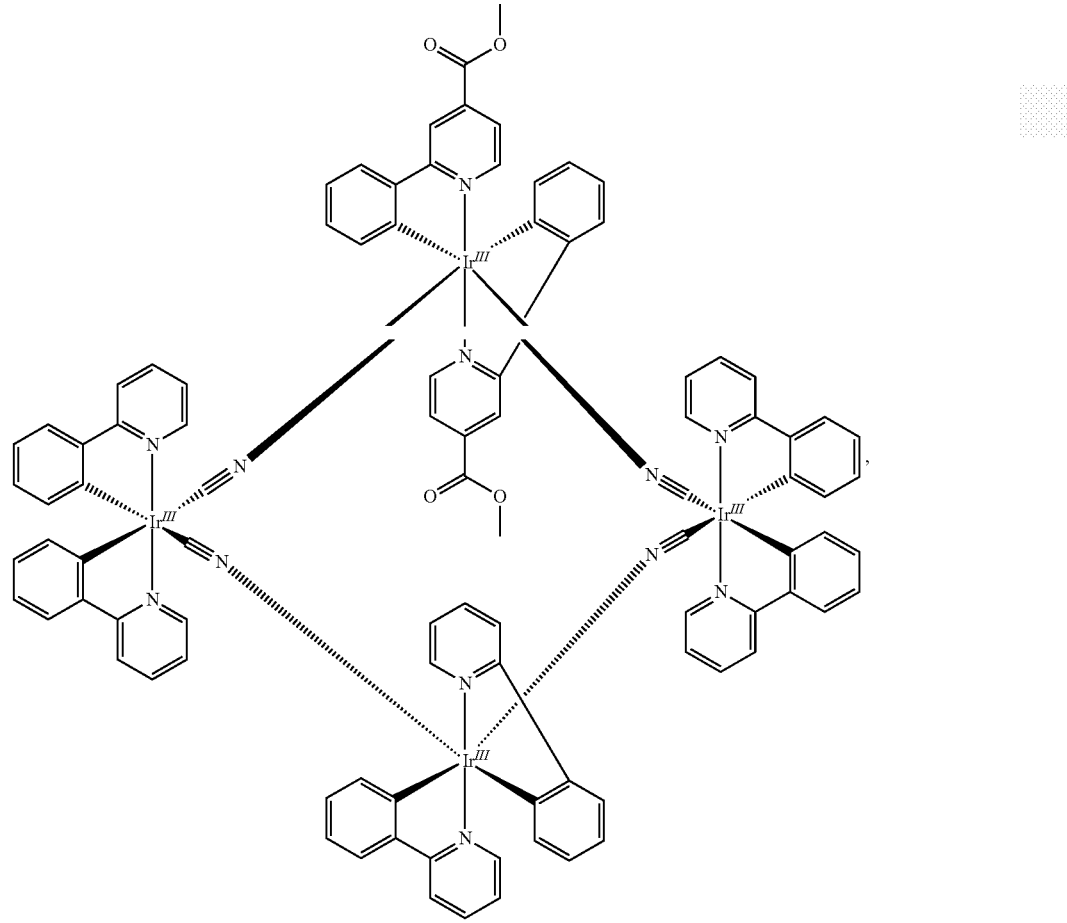

-continued
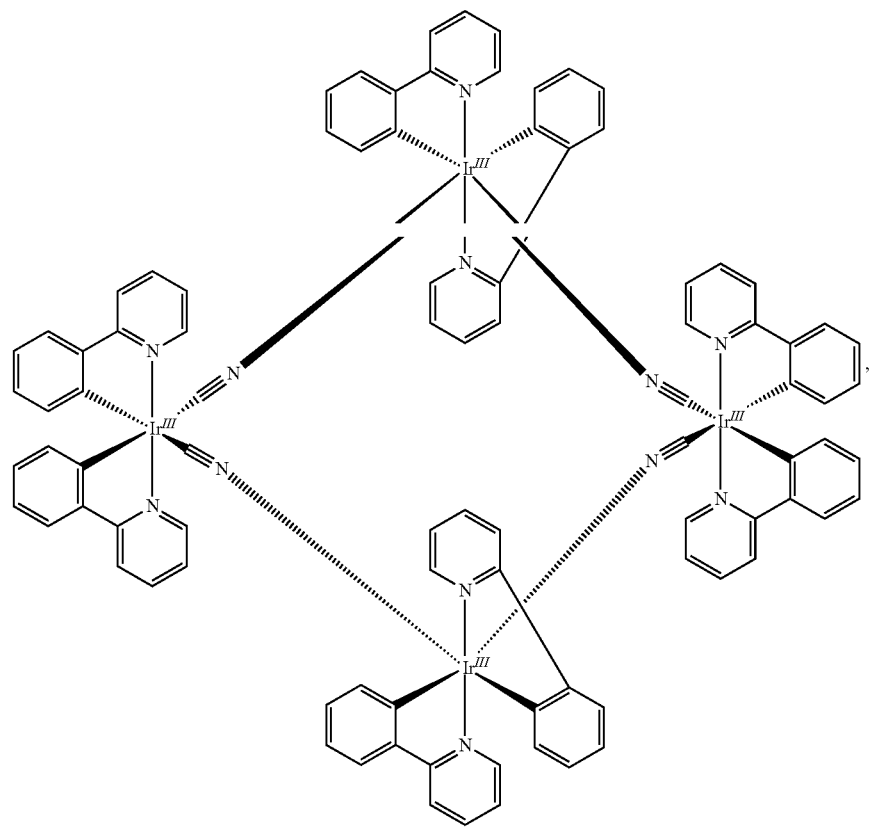
Formula (IX)
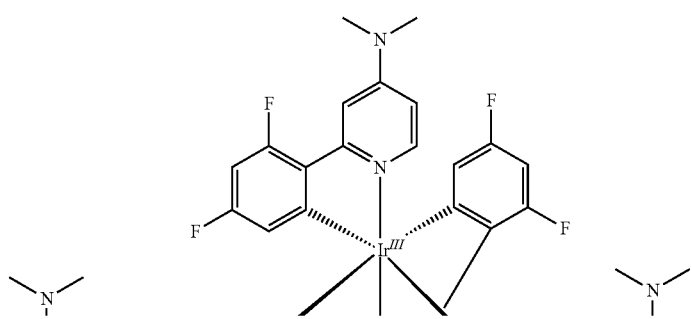
Formula (X)

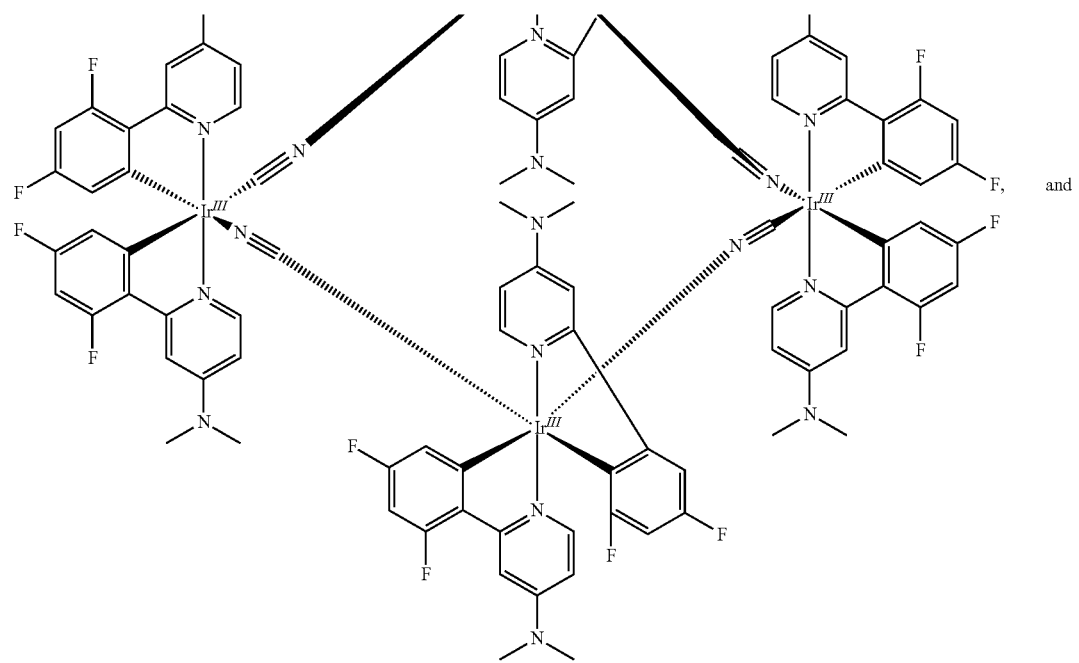
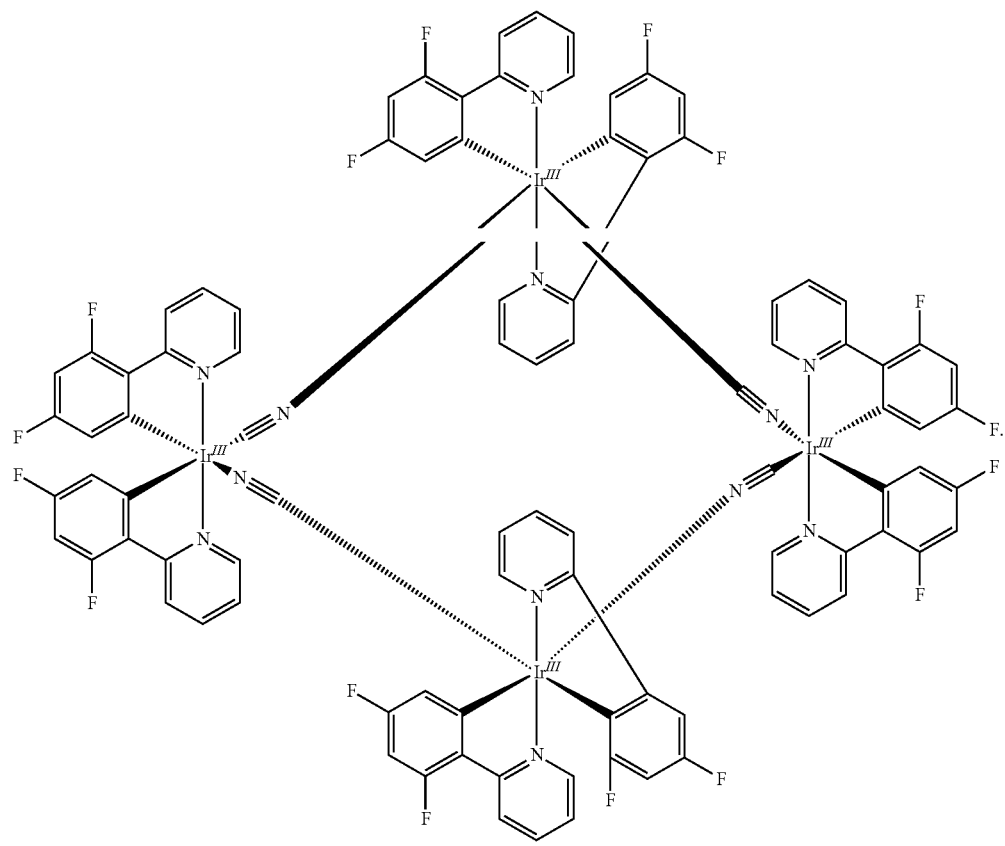
Formula (XI)

Formula (XII)

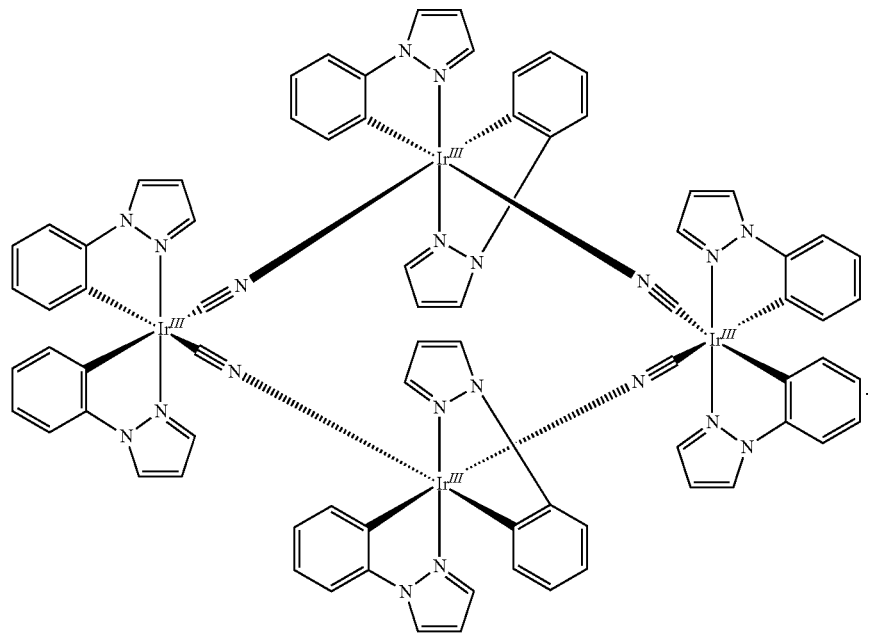

Excellent results can be obtained with light emitting materials comprising the above complexes of Formulae (VI) to (XII). Complexes of Formulae (VI) to (XII) comprising orthometallated ligands and a cyano bridged ligand are particularly advantageous due to their broad and intense emission in the various wavelength regions which is necessary for white light emission.

The synthesis of the complexes of Formula (I), i.e., metal complex comprising two orthometallated ligands (C^N ligands) and bridged ligands ($B_1$ and $B_2$), can be accomplished by any known method. The synthetic methods suitable for the preparation of the complexes of Formula (I) are described in detail in K. Dedian et al, *Inorg. Chem.*, 30:1685 (1991); F. O. Garces, K. A. King, and R. J. Watts, *Inorg. Chem.*, 27:3464 (1988); M. G. Colombo, et al, *Inorg. Chem.*, 33:545 (1994); J H van Diemen, J G Haasnoot, R. Hage, E. Miiller and J. Reedijk, *Inorg. Chem. Acta*, 181:245 (1991); K. A. King, et al., *J. Am. Chem. Soc.*, 107:1431 (1985), which are hereby incorporated by reference in their entirety.

Generally, an example of the multinuclear complexes of the present invention, such as tetranuclear complexes of Formula (I), can be prepared according to the following reaction scheme:

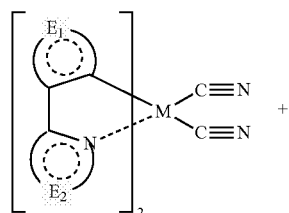

[C^N]$_2$M(CN)$_2$(X)

+

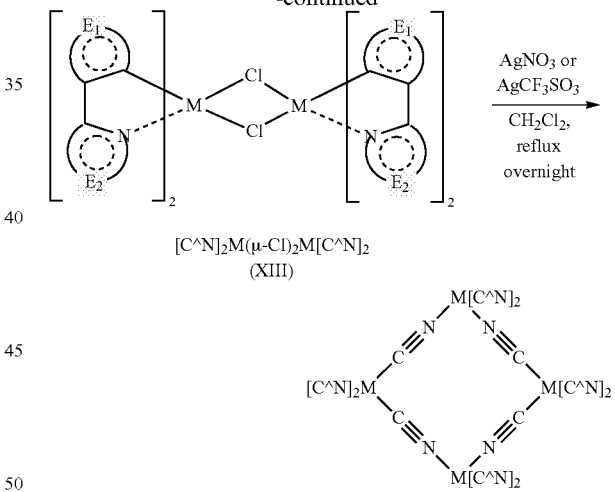

[C^N]$_2$M(μ-Cl)$_2$M[C^N]$_2$
(XIII)

$\xrightarrow[\text{CH}_2\text{Cl}_2, \text{ reflux overnight}]{\text{AgNO}_3 \text{ or AgCF}_3\text{SO}_3}$

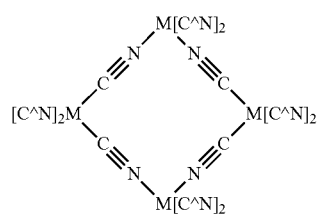

Orthometallated ligands (H—C^N) can be prepared with good to excellent yields by using Suzuki coupling of the substituted pyridine compound with corresponding arylboronic acids, as described in LOHSE et al., "The Palladium Catalyzed Suzuki Coupling of 2- and 4-chloropyridines," *Syn. Lett.*, 1:15-18 (1999) and in U.S. Pat. No. 6,670,645, which are hereby incorporated by reference in their entirety.

Synthetic methods, which are particularly adapted for the preparation of fluorinated orthometallated ligands (H—C^N), are described in Japanese Patent Publication Nos. 2003113164 A and 2003113163 A, which are hereby incorporated by reference in their entirety.

If the transition metal is iridium, trihalogenated iridium (III) compounds such as IrCl$_3$·H$_2$O, hexahalogenated iridium (III) compounds such as $M^o{}_3 IrX^o{}_6$, wherein $X^o$ is a halogen, specifically Cl and M° is an alkaline metal, specifically K, and hexahalogenated iridium (IV) compounds such as M°$_2$IrX°$_6$, wherein X° is a halogen, specifically Cl and M° is an alkaline metal, specifically K (Ir halogenated precursors) can be used as starting materials to synthesize the complexes of the present invention.

[C^N]$_2$Ir(CN)$_2$ (compound X, wherein M=Ir) complexes can be prepared by the reaction of [Ir(ppy)$_2$(Cl)]$_2$ (ppy=2-phenylpyridine) with tetraalkylammonium cyanide, as described in NAZEERUDDIN et al. "Highly phosphorescent iridium complexes and their application in organic light-emitting devices," J. Am. Chem. Soc. 125(29):8790-8797 (2003), which is hereby incorporated by reference in its entirety.

[C^N]$_2$Ir(μ-X°)$_2$Ir[C^N]$_2$ complexes (compound XIII, wherein M=Ir), with X° being a halogen, specifically Cl (e.g., [(2-(2,4-difluorophenyl)-4-dimethylaminopyridine)$_2$IrCl]$_2$, [(2-(2,4-difluorophenyl)pyridine)$_2$IrCl]$_2$, [(2-phenylpyridine)$_2$IrCl]$_2$ and [(2-(2,4-difluorophenyl)-5-dimethylaminopyridine)$_2$IrCl]$_2$) can be prepared from said Ir halogenated precursors and the appropriate orthometalated ligand by resorting to procedures known in the literature, as described in King and Watts, J. Am. Chem. Soc. 109:1589-1590 (1987), which is hereby incorporated by reference in its entirety.

The preparation of tetranuclear complexes by reacting [C^N]$_2$M(CN)$_2$ and) [C^N]$_2$M(μ-X°)$_2$M[C^N]$_2$ is advantageously carried out in organic solvents. Polar aprotic solvents are generally used for this reaction. A solvent which gives particularly good results is methylene dichloride (CH$_2$Cl$_2$). The solvent can be used as such or in admixture with another solvent.

The reaction can be conducted at a temperature of from 0 to 100° C., specifically 20 to 80° C., more specifically 40 to 50° C., most specifically at the refluxing temperature of methylene dichloride, for 0.5 to 48 hours, specifically 2 to 24 hours, most specifically 4 to 12 hours.

The reaction can be carried out in the presence of a suitable metal salt, such as silver salts with non- or weakly-coordinating counterions, e.g., silver tetrafluoroborate (AgBF$_4$) and silver hexafluorophosphate (AgPF$_6$), particularly silver nitrate (AgNO$_3$) or silver triflate (AgCF$_3$SO$_3$).

The present invention also relates to using the light emitting material comprising the multinuclear complexes, as described above, in the emitting layer of an organic light emitting device (OLED).

Furthermore, the present invention relates to using the light emitting material comprising the multinuclear complexes, as described above, as a dopant in a host layer, under conditions effective to function as an emissive layer in an organic light emitting device.

If the light emitting material is used as a dopant in a host layer, it is generally used in an amount of at least 1% wt, specifically of at least 3% wt, more specifically of at least 5% wt with respect to the total weight of the host and the dopant, and generally at most 25% wt, specifically at most 20% wt, more specifically at most 15% wt.

The present invention also relates to an organic light emitting device (OLED) comprising an emissive layer (EML). The emissive layer comprises the light emitting material, as described above, optionally with a host material (wherein the light emitting material is specifically present as a dopant). The host material is notably adapted to luminesce when a voltage is applied across the device structure.

An OLED generally comprises:

a glass substrate;

an anode, which is a generally transparent anode such as an indium-tin oxide (ITO) anode;

a hole transporting layer (HTL);

an emissive layer (EML);

an electron transporting layer (ETL); and a cathode, which is generally a metallic cathode such as an Al layer.

As for a hole conducting emissive layer, one may have an exciton blocking layer, notably a hole blocking layer (HBL) between the emissive layer and the electron transporting layer. As for an electron conducting emissive layer, one may have an exciton blocking layer, notably an electron blocking layer (EBL) between the emissive layer and the hole transporting layer. The emissive layer may be equal to the hole transporting layer (in which case the exciton blocking layer is near or at the anode) or to the electron transporting layer (in which case the exciton blocking layer is near or at the cathode).

The emissive layer may be formed with a host material in which the above-described light emitting material resides as a guest or the emissive layer may consist essentially of the light emitting material. In the &inner case, the host material may be a hole-transporting material selected from the group of substituted tri-aryl amines. Specifically, the emissive layer is formed with a host material in which the light emitting material resides as a guest. The host material may be an electron-transporting material selected from the group consisting of metal quinoxolates (e.g., aluminium quinolate (Alq$_3$), lithium quinolate (Liq)), oxadiazoles, and triazoles. An example of a host material is 4,4'-N,N-dicarbazole-biphenyl ["CBP"], which has the following formula:

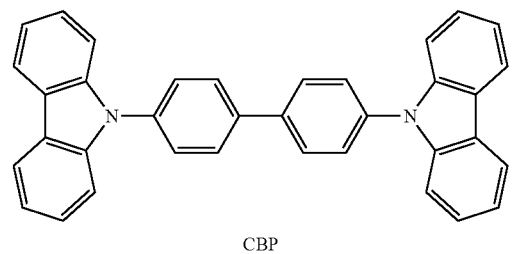 [SMILES: c1ccc2c(c1)c1ccccc1n2-c1ccc(-c2ccc(-n3c4ccccc4c4ccccc43)cc2)cc1 ; "CBP"]

CBP

Optionally, the emissive layer may also contain a polarization molecule, which is present as a dopant in said host material and having a dipole moment, that generally affects the wavelength of light emitted when said light emitting material used as a dopant luminesces.

A layer formed of an electron transporting material is advantageously used to transport electrons into the emissive layer comprising the light emitting material and the (optional) host material. The electron transporting material may be an electron-transporting matrix selected from the group consisting of metal quinoxolates (e.g., Alq$_3$, Liq), oxadiazoles and triazoles. An example of an electron transporting material is tris-(8-hydroxyquinoline)aluminium of formula ["Alq$_3$"]:

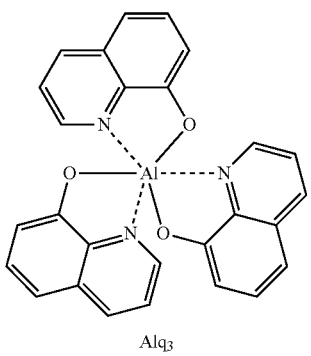

Alq3

A layer formed of a hole transporting material is advantageously used to transport holes into the emissive layer comprising the above-described light emitting material and the (optional) host material. An example of a hole transporting material is 4,4'-bis[N-(1-naphthyl)-N-phenylamino]biphenyl ["α-NPD"].

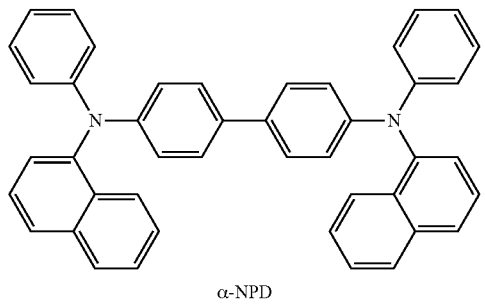 [SMILES: c1ccc(N(c2ccc(-c3ccc(N(c4ccccc4)c4cccc5ccccc45)cc3)cc2)c2cccc3ccccc23)cc1 ; "a-NPD"]

α-NPD

An exciton blocking layer ("barrier layer") can be used to confine excitons within the luminescent layer ("luminescent zone"). As for a hole-transporting host, the blocking layer may be placed between the emissive layer and the electron transport layer. An example of a material, which is used for such a barrier layer, is 2,9-dimethyl-4,7-diphenyl-1,10-phenanthroline (also called bathocuproine or "BCP") having the following formula:

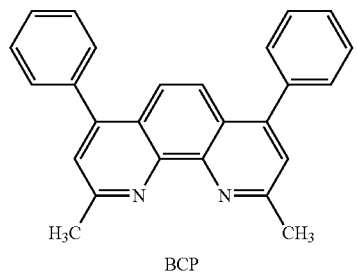

BCP

Specifically, the OLED may have a multilayer structure, as depicted in FIG. 1, wherein: 1 is a glass substrate; 2 is an ITO layer; 3 is a HTL layer comprising a-NPD; 4 is an EML comprising CBP as a host material and the light emitting material as a dopant in an amount of about 8% wt with respect to the total weight of the host and dopant; 5 is a HBL comprising BCP; 6 is an ETL comprising $Alq_3$; and 7 is an Al layer cathode.

Another aspect of the present invention relates to a display device comprising the above OLED.

EXAMPLES

Example 1

Synthesis of Multinuclear Complexes

Cyclometalated Ir(III) m-chloro-bridge dimer with ligand (L), bis-cyclometalated $Ir(III)(L)_2(CN)_2TBA$ and $Ir(III)(L)_2$(acetonitrile)$_2CF_3SO_2$ were obtained as described in the literatures which are cited herein.

Preparation of Homoleptic Complexes

The homoleptic multinuclear complexes, such as Formulae (X) and (XI), were prepared as shown below.

Method 1:

In a 250 mL two-necked round bottom flask equipped with a condenser were placed an $[(L)_2Ir(m-Cl)_2Ir(L)_2]$ complex (about 200 mg depending on the complex, 1 equivalent), tetrabutyl ammonium cyanide (1.9 equivalent) and silver (I) trifluoromethane sulfonate (2.2 equivalents), and dichloromethane (200 mL). The flask was evacuated and filled with argon gas three times. The reaction mixture was refluxed for 8 hours under argon gas and cooled to room temperature. The reaction mixture was filtered with a short silica gel pad and subsequently washed with dichloromethane or a dichloromethane/methanol 3% mixture. The solvents were removed under vacuum and the complex further purified by a Sephadex chromatography column. The main band was collected, concentrated under vacuum, and precipitated with hexane. The precipitate was filtered with fritted glass, washed with hexane, and dried to yield the expected tetranuclear complex in 30-70% yield as a solid.

Method 2:

In a 250 mL two-necked round bottom flask equipped with a condenser were placed an $Ir(III)(L)_2(CN)_2TBA$ complex (about 200 mg depending on the complex, 1 equivalent), $Ir(III)(L)_2$(acetonitrile)$_2CF_3SO_2$ (about 200 mg depending on the complex, 1 equivalent) and dichloromethane (200 mL) The flask was evacuated and filled with argon gas three times. The reaction mixture was refluxed for 8 hours under argon gas and cooled to room temperature. The reaction mixture was filtered with a short silica gel pad and subsequently washed with dichloromethane or a dichloromethane/methanol 3% mixture. The solvents were removed under vacuum and the complex further purified by a Sephadex chromatography column. The main band was collected, concentrated under vacuum, and precipitated with hexane. The precipitate was filtered with fritted glass and washed with hexane and dried to yield the expected tetranuclear complex in 30-70% yield as a solid.

Preparation of Heteroleptic Complexes

The heteroleptic multinuclear complexes, such as Formulas (VII) and (VIII), are prepared in the same manner as shown below.

$$\text{Type}[Ir(L)_2][Ir(L')_2][Ir(L)_2][Ir(L')_2]: \qquad 1$$

Method 3:

Method 2 for the homoleptic complexes synthesis was used with $Ir(III)(L)_2(CN)_2TBA$ and $Ir(III)(L')_2$(acetonitrile)$_2$$CF_3SO_2$ as starting material.

Method 4:

In a 250 mL two-necked round bottom flask equipped with a condenser were placed an $[(L)_2Ir(m-Cl)_2Ir(L)_2]$ complex (about 200 mg depending on the complex, 0.5 equivalent), $Ir(III)(L)_2(CN)_2TBA$ complex (about 100 mg depending on the complex, 1 equivalent) and silver (I) trifluoromethane sulfonate (1.2 equivalent), and dichloromethane (200 mL). The flask was evacuated and filled with argon gas three times. The reaction mixture was refluxed for 8 hours under argon gas and cooled to room temperature. The reaction mixture was filtered with a short silica gel pad and subsequently washed with dichloromethane or a dichloromethane/methanol 3% mixture. The solvents were removed under vacuum and the complex further purified by a Sephadex chromatography column. The main band was collected, concentrated under vacuum, and precipitated with hexane. The precipitate was filtered with fritted glass, washed with hexane, and dried to yield the expected heteroleptic tetranuclear complex in 20-70% yield as a solid.

Type[Ir(L)$_2$][Ir(L')$_2$][Ir(L)$_2$][Ir(L")$_2$]: 2

Method 5:

In a 250 mL two-necked round bottom flask equipped with a condenser were placed an [(L')$_2$Ir(m-Cl)$_2$Ir(L')$_2$] complex (about 100 mg depending on the complex, 0.25 equivalent), [(L)$_2$Ir(m-Cl)$_2$Ir(L)$_2$] complex (about 200 mg depending on the complex, 0.5 equivalent), [(L")$_2$Ir(m-Cl)$_2$Ir(L")$_2$] complex (about 100 mg depending on the complex, 0.25 equivalent), tetrabutyl ammonium cyanide (1.9 equivalent) and silver (I) trifluoromethane sulfonate (2.2 equivalent), and dichloromethane (200 mL). The flask was evacuated and filled with argon gas three times. The reaction mixture was refluxed for 8 hours under argon gas and cooled to room temperature. The reaction mixture was filtered with a short silica gel pad and subsequently washed with dichloromethane or a dichloromethane/methanol 3% mixture. The solvents were removed under vacuum and the complex further purified by a Sephadex chromatography column. The main bands were collected, concentrated under vacuum, and precipitated with hexane. The precipitate was filtered with fritted glass, washed with hexane, and dried to yield different combinations of the expected tetranuclear complexes in 5-10% yield each, as solids.

Method 6:

First step: In a 250 mL two-necked round bottom flask equipped with a condenser were placed an Ir(III)(L)$_2$(CN)$_2$TBA complex (about 200 mg depending on the complex, 3 equivalents), Ir(III)(L')$_2$(acetonitrile)$_2$CF$_3$SO$_2$ (about 60 mg depending on the complex, 1 equivalent) and dichloromethane (200 mL). The flask was evacuated and filled with argon gas three times. The reaction mixture was refluxed for 8 hours under argon gas and cooled to room temperature. The reaction mixture was filtered with a short silica gel pad and subsequently washed with dichloromethane or a dichloromethane/methanol 3% mixture. The solvents were removed under vacuum and the complex further purified by a Sephadex chromatography column. The main band was collected, concentrated under vacuum and precipitated with hexane. The precipitate was filtered with fritted glass, washed with hexane, and dried to yield the expected non-closed trinuclear complex [Ir(L)$_2$][Ir(L')$_2$][Ir(L)$_2$] in 30-70% yield as a solid.

Second step: In a 250 mL two-necked round bottom flask equipped with a condenser were placed an [Ir(L)$_2$] [Ir(L')$_2$] [Ir(L)$_2$] complex (about 200 mg depending on the complex, 1 equivalent), Ir(III)(L")$_2$(acetonitrile)$_2$CF$_3$SO$_2$ (about 60 mg depending on the complex, 1 equivalent) and dichloromethane (200 mL) The flask was evacuated and filled with argon gas three times. The reaction mixture was refluxed for 8 hours under argon gas and cooled to room temperature. The reaction mixture was filtered with a short silica gel pad and subsequently washed with dichloromethane or a dichloromethane/methanol 3% mixture. The solvents were removed under vacuum and the complex further purified by a Sephadex chromatography column. The main band was collected, concentrated under vacuum and precipitated with hexane. The precipitate was filtered with fritted glass and washed with hexane and dried to yield the expected tetranuclear complex [Ir(L)$_2$][Ir(L')$_2$][Ir(L)$_2$][Ir(L")$_2$] in 30-70% yield as a solid.

A. Preparation of the Compounds of Formula (IX): [Ir(phenyl-pyridine)$_2$(CN)]$_4$ For the preparation of the multinuclear complex of Formula (IX), only one type of iridium complex is employed to obtain a homoleptic tetranuclear complex according to the scheme below (Method 1).

Scheme 1. One-pot synthetic scheme for multinuclear iridium complex Formula (IX).

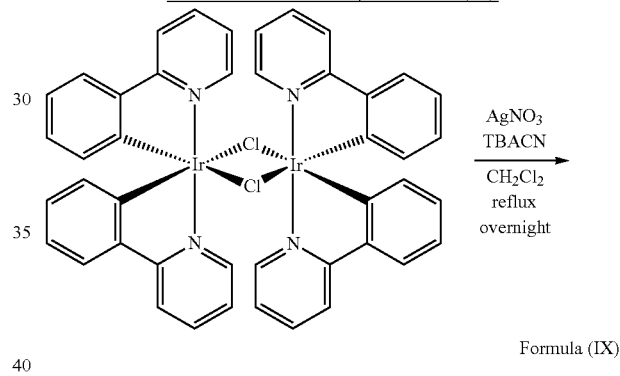

Formula (IX)

The compound of Formula (IX) was obtained as a bright green luminescent yellow solid with a 68% yield. MS: m/z: 1054.6112 (calcd. 1054.6986 for [MH]$^{2+}$)

B. Preparation of the Compounds of Formula (X): [Ir(2-(2,4-difluoro-phenyl)-4-NMe$_2$-pyridine)$_2$(CN)]$_4$

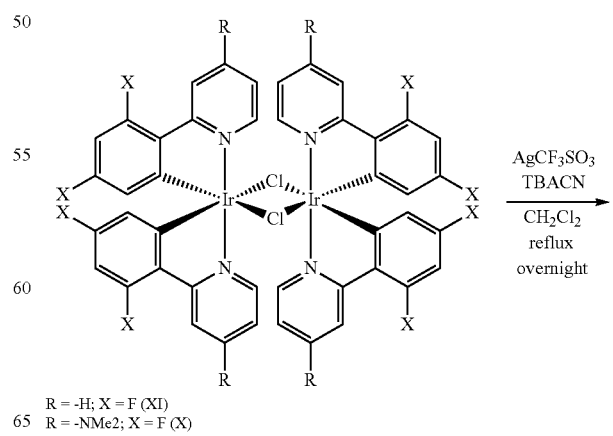

R = -H; X = F (XI)
R = -NMe2; X = F (X)

The compound of Formula (X) was prepared according to Method 1. After filtration and washing with hexane, a bright light-blue luminescent pale yellow solid was obtained with a 29% yield.

C. Preparation of the Compounds of Formula (VI): [Ir(2-phenyl-4-COOMe-pyridine)$_2$(CN)]$_4$ The compound of Foimula (VI) was prepared according to Method 1. After filtration and washing with hexane, a bright orange luminescent red solid was obtained with a 46% yield.

D. Preparation of the Compounds of Formula (XI): [Ir(2-(2, 4-difluoro-phenyl)-pyridine)$_2$(CN)]$_4$ The compound of Formula (XI) was prepared according to Method 1. After filtration and washing with hexane, a light blue luminescent pale yellow solid was obtained with a 54% yield.

E. Preparation of the Compounds of Formula (XII): [Ir(1-phenyl-pyrazolyl)$_2$(CN)]$_4$ The compound of Formula (XII) was prepared according to Method 1. After filtration and washing with hexane, a bright light green luminescent colorless solid was obtained with a 38% yield.

F. Preparation of the Compounds of Formula (VII): [Ir(2-phenyl-pyridine)$_2$(CN)$_2$][Ir(2-phenyl-4-COOMe-pyridine)$_2$][Ir(2-phenyl-pyridine)$_2$(CN)$_2$][Ir(2-phenyl-4-COOMe-pyridine)$_2$]

The compound of Formula (VII) was prepared according to Method 4, using [(2-phenyl-4-COOMe-pyridine)$_2$Ir(μ-Cl)$_2$Ir(2-phenyl-4-COOMe-pyridine)$_2$] complex and Ir(III)(2-phenyl-pyridine)$_2$(CN)$_2$TBA obtained as a bright orange luminescent orange solid in a 31% yield. MS: m/z=1169.1785 (calcd. 1169.7056 [M-H]$^{2+}$).

G. Preparation of the Compounds of Formula (VIII): [Ir(2-phenyl-pyridine)$_2$(CN)$_2$][Ir(2-phenyl-4-COOMe-pyridine)$_2$][Ir(2-phenyl-pyridine)$_2$(CN)$_2$][Ir(2-phenyl-pyridine)$_2$]

The compound of Formula (VIII) was prepared according to Method 6, using Ir(III)(2-phenyl-4-COOMe-pyridine)$_2$(acetonitrile)$_2$CF$_3$SO$_2$ complex and Ir(III)(2-phenyl-pyridine)$_2$(CN)$_2$TBA in the first step and the Ir(III)(2-phenyl-pyridine)$_2$(acetonitrile)$_2$CF$_3$SO$_2$ complex in the second step, and obtained as a bright orange luminescent orange solid in 22% yield. MS: m/z=1111.0532 (calcd. 1111.7001 [M-H]$^{2+}$).

Scheme 2. Synthetic scheme of the multinuclear iridium complex of Formulae (VII) and (VIII)

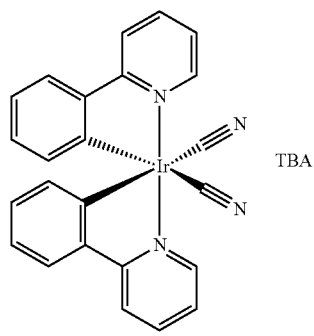

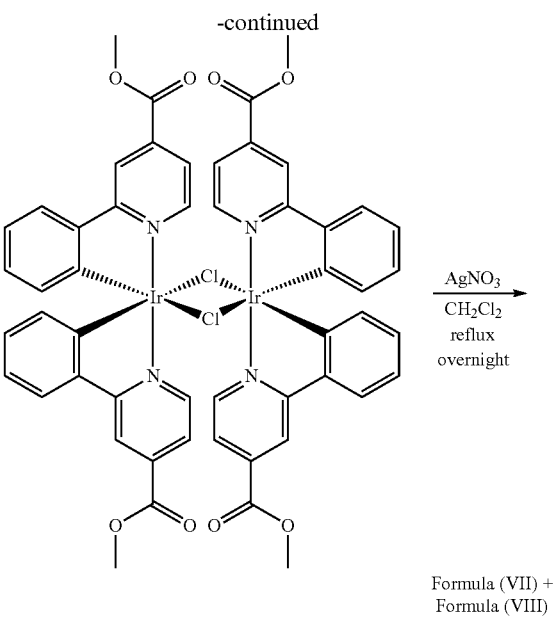

Formula (VII) + Formula (VIII)

Figure 2:
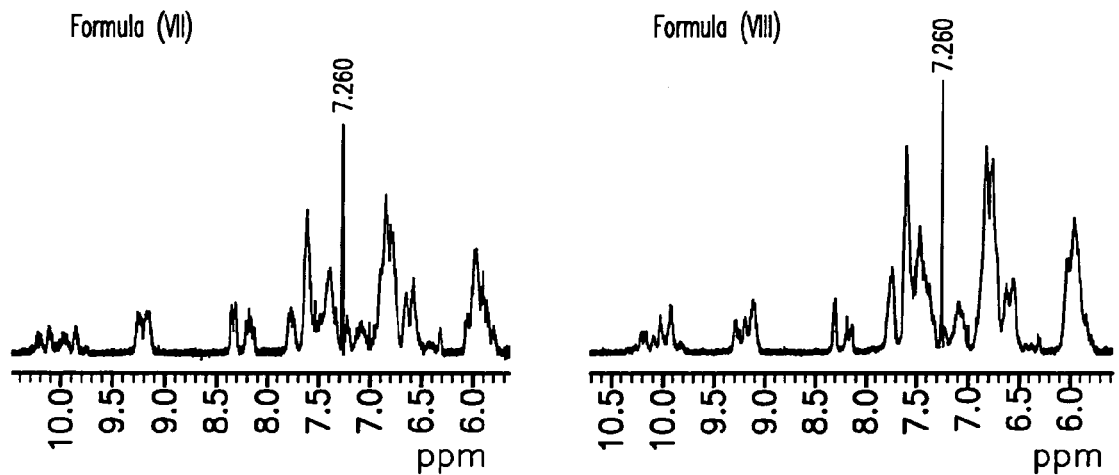
FIG. 2 shows the 1H-NMR spectra of a mixture containing the complexes of Formulae (VII) and (VIII) of the present invention.

The crude obtained was apparently highly luminescent, in particular in the solid state compared to the usual iridium complexes. However, the thin layer chromatography (TLC) analysis showed several defined spots, where the two main spots were separated by column chromatography as Formula (VII) and Formula (VIII). The $^1$H-NMR of those fractions were very complex but different from each other (see FIG. 2), and no tetrabutylammonium cation was observed (not shown).

Figure 3:
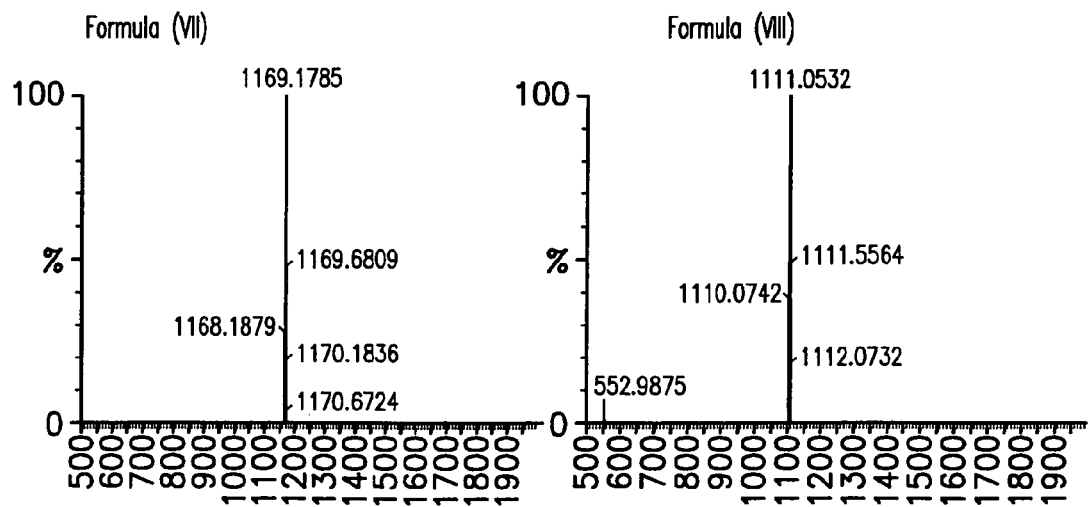
FIG. 3 shows the mass spectrogram of the complexes of Formulae (VII) and (VIII) of the present invention.

Surprisingly, the mass spectrometry results showed a very clean product, with only one peak in each fraction corresponding to a double charged compound: Formula (VII) m/z=1169.18 and Formula (VIII) m/z=1111.05 (see FIG. 3). After a column purification of the main spot, the $^1$H-NMR and mass spectrometry analysis results were very similar to those of Formulae (VII) and (VIII) with a broad and complicated $^1$H NMR and a single peak in mass spectrometry.

Example 2

Crystal Structure of Multinuclear Complexes

Figure 4:
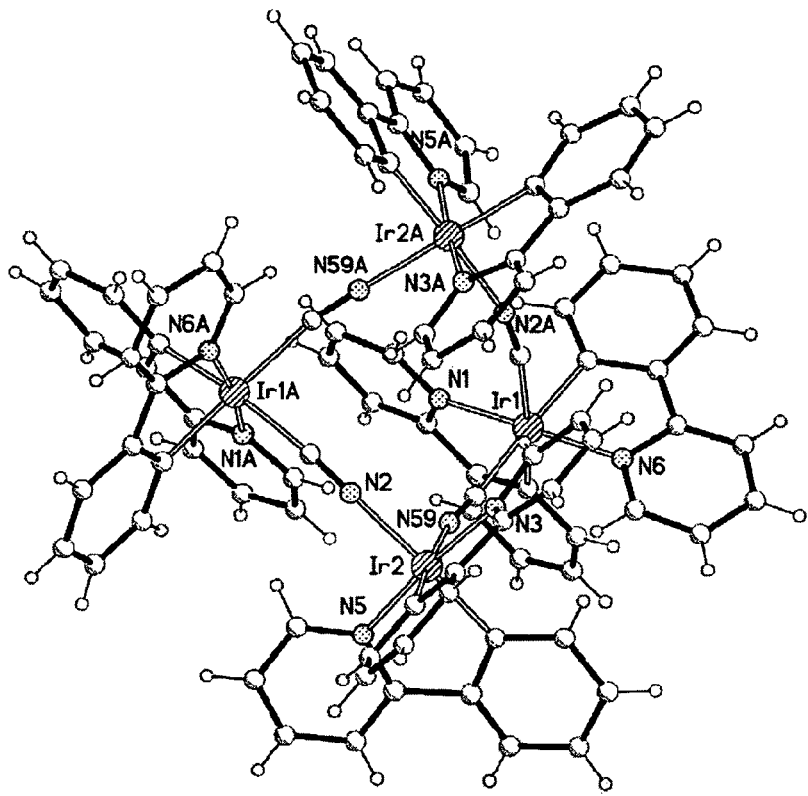
FIG. 4 illustrates the X-ray crystal structure of the complex of Formula (IX) of the present invention where the four iridium centers are connected through cyanide bridges.
Figure 5:
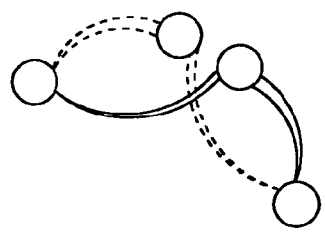
FIG. 5 shows a schematic perspective representation of iridium having bridged cyanides according to the present invention.

Crystals of the compound of Formula (IX) for X-ray analysis were successfully obtained by slow diffusion of methanol into an acetonitrile solution of Formula (IX). The crystal structure and a schematic drawing of the iridium centers are illustrated in FIGS. 4 and 5, respectively.

The crystal structure results showed that the compound was indeed a tetranuclear iridium complex bridged by cyanides, where it was not a square, but rather intermediate between a square and a tetrahedral. In this organization, the cyanide bridges are not bridging two iridium atoms in a linear fashion, but their distorted coordination leads to curves between two iridium atoms as shown in the schematic representation. Another way to look at this structure is to see it as two non-coplanar triangles attached by one side. This structure is sometimes called a "butterfly" in chemistry, and therefore this new family of molecules can be named as "iridium-butterflies."

It should be noted that the coordination of the cyanide bridge leads to two different iridium complexes-type in the square: two iridium centres are coordinated with two nitrogen atoms of the cyanide bridges, and the two other iridium centres are connected with two carbon atoms of the cyanide bridge. However, due to the quality of the crystals used in the X-ray analysis, another coordination pattern where all four iridium centres are coordinated with one nitrogen atom and one carbon atom may be formed. According to the data, the structures of other compounds of the present invention, such as Formulas (VII), (VIII), (X), and (XI), may have almost identical structures to Formula (IX), i.e., the butterfly structure.

Example 3

Photophysical Results

Figure 6:
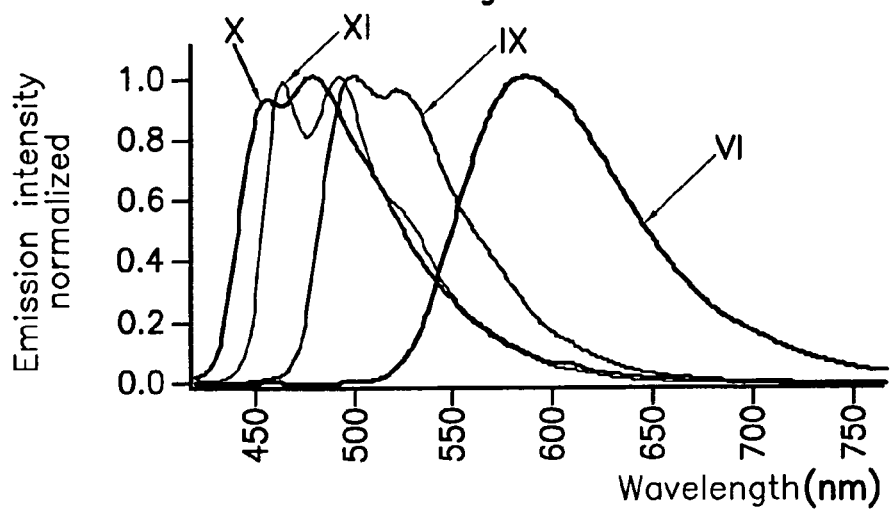
FIG. 6 shows the photoluminescence emission spectra of some butterfly molecules in CH2Cl2 excitation 400 nm, namely from right to left: Formula (VI); Formula (VII); Formula (VIII); Formula (IX).
Figure 7:
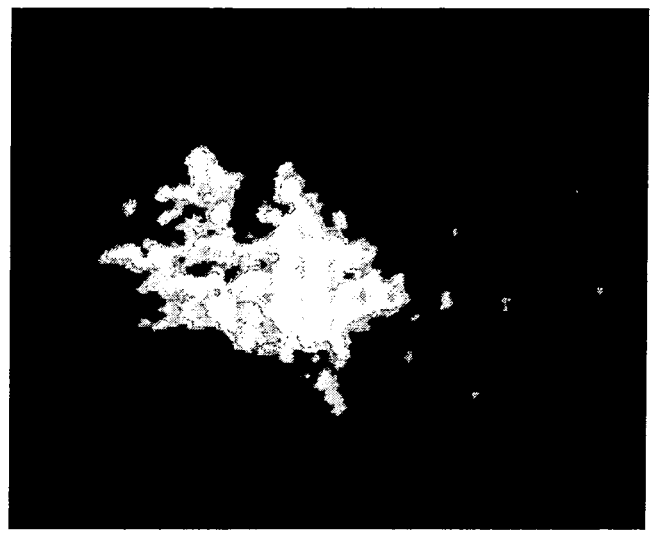
FIG. 7 shows a solid-state emission of the complex of Formula (IX) of the present invention producing a strong green luminescence.
Figure 8:
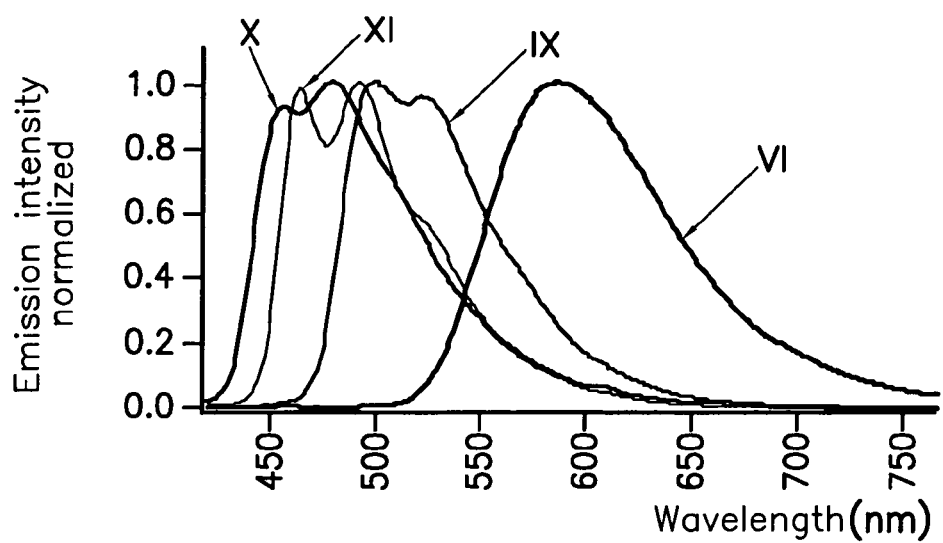
FIG. 8 shows the emission spectra of various complexes of the present invention in non-degassed dichloromethane: from left to right, Formula (X); Formula (XI); Formula (IX); Formula (VI).
Figure 9:
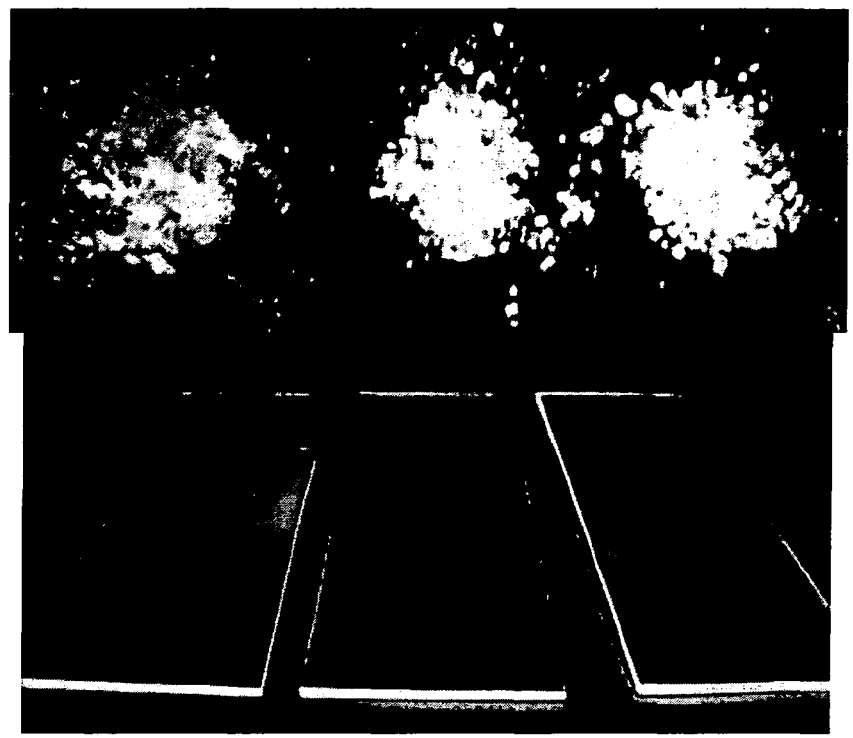
FIG. 9 shows a solid-state emission and in PMMA films luminescence of various complexes of the present invention: from left to right, Formula (X); Formula (IX); Formula (VIII).

The photoluminescence quantum yield of Formula (IX) has been measured in acetonitrile and is fairly high, i.e., Φ=66%. In addition, the solid state luminescences for Formulae (VII), (VIII), and (IX), are easily seen with a naked eye, which points to possibly high quantum yield in the solid state (see FIG. 6). In particular, Formula (IX) clearly shows strong green luminescence in the solid state (see FIG. 7). In sum, the photophysical results in $CH_2Cl_2$ with an excitation at 400 nm are as follows: Formula (IX): λmax=498 nm, the full width at half maximum (fwhm)=80 nm; Formula (VII): λmax=573 nm, fwhm=124 nm; Formula (VIII): λmax=578 nm, fwhm=105 nm. The solid state-luminescence is fair for Formula (X), very weak for Foimula (XI) (not shown), strong for Formula (IX), and very strong for Formula (VIII) (see FIGS. 8 and 9).

The four iridium centres which are "caged" by the phenyl pyridine ligands and the overall structure of the complexes of the present invention being certainly rigid as seen with the NMR analysis, can explain such observation of strong luminescence in the solid state. This makes this new family of phosphorescent molecules potentially interesting for solid-state devices.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

Example 4

OLED Results with Formula IX

Spincoated OLEDs
OLED structure:
ITO/CH8000/PVK:OXD7:Formula IX/TPBi/Cs2CO3/Al
Comparative OLED structure:
ITO/CH8000/PVK:PBD: Ir(mppy)3/TPBi/Cs2CO3/Al
Experimental Part.
OXD-7 (1,3-Bis[(p-tert-butyl)phenyl-1,3,4-oxadiazoyl]benzene) and PBD (2-(4-biphenylyl-5-(4-tertbutylphenyl)-1,2,3-oxadiazole) were obtained from Luminescence Technology Corp.
Poly(9-vinylcarbazole) (PVK, Mw=1.100.00) has been obtained from SP2.
Poly(3,4-ethylenedioxythiophene):poly(styrenesulfonate) (PEDOT:PSS, Clevios CH8000) and 1,3,5-tris[N-(phenyl)benzimidazole]benzene (TPBI) were purchased from HC Starck and from Luminescence Technology Corp. respectively. The device structure consists of a 120 nm transparent ITO layer as the bottom electrode, supported on a glass substrate. A PEDOT:PSS layer and the emissive layer were spun in sequence on top of ITO, using a Delta6 RC spincoater from Suss Microtec. Then, TPBI, Cs2CO3 and the aluminum top metal contact were evaporated in sequence using a Lesker Spectros system. The ITO surface was treated for 10 min with O2-plasma cleaner prior to any further processing. The emissive layer was spun from a chlorobenzene solution containing PVK:OXD7 and different mass ratios of Formula IX. The OLEDs were characterized optically and electrically with a C9920-12 External Quantum Efficiency Measurement System from HAMAMATSU.

Results Summary

At 100 Cd/m2, the external quantum efficiency with the device containing 3% of Foiinula IX was 10.1%, with current and power efficiency of 31.6 Cd/A and 19 lm/W, respectively. However, negligible difference was found in the concentration range of 4-10%. For these devices the turn-on voltage is about 3.5 V. By comparison with another device having the same architecture and benchmark molecule Ir(mppy)3 in place of Formula IX, an improvement of the overall performances is evident. In Table 1, the performances of the devices with Formula IX vs Ir(mppy)3 measured at 100 and 1000 Cd/m2 are reported.

TABLE 1

| | 100 Cd/m2 | | | | 1000 Cd/m2 | | | |
|---|---|---|---|---|---|---|---|---|
| | V | EQE | Lm/W | Cd/A | V | EQE | Lm/W | Cd/A |
| Formula IX 1% | 5.1 | 9.1 | 17.6 | 28.6 | 7.2 | 8.2 | 11.0 | 25.4 |
| Formula IX 3% | 5.2 | 10.1 | 19.0 | 31.6 | 7.4 | 9.3 | 12.4 | 29.0 |
| Ir(mppy)3 1% | 7 | 8.84 | 13.88 | 31.23 | 9.3 | 8.37 | 9.87 | 29.39 |

Figure 10:
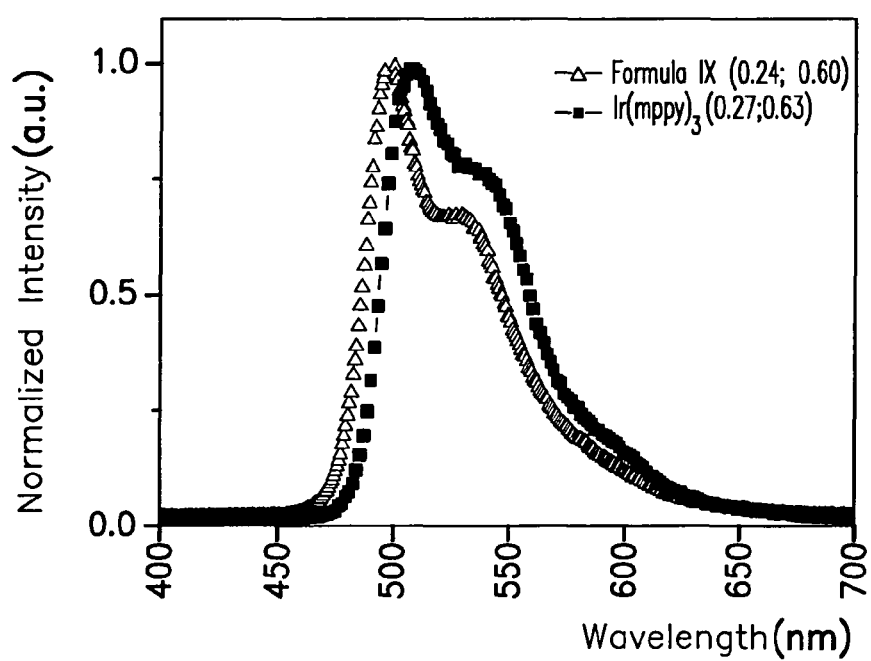
FIG. 10 shows the normalized emission spectra of Formula IX and benchmark molecule Ir(mppy)3, together with the corresponding CIE coordinates.

The normalized EL spectra of Formula IX and benchmark molecule Ir(mppy)3 [tris(2-(p-tolyl)pyridine)iridium(III)] are depicted in FIG. 10, together with the corresponding CIE coordinates.

Figure 11:
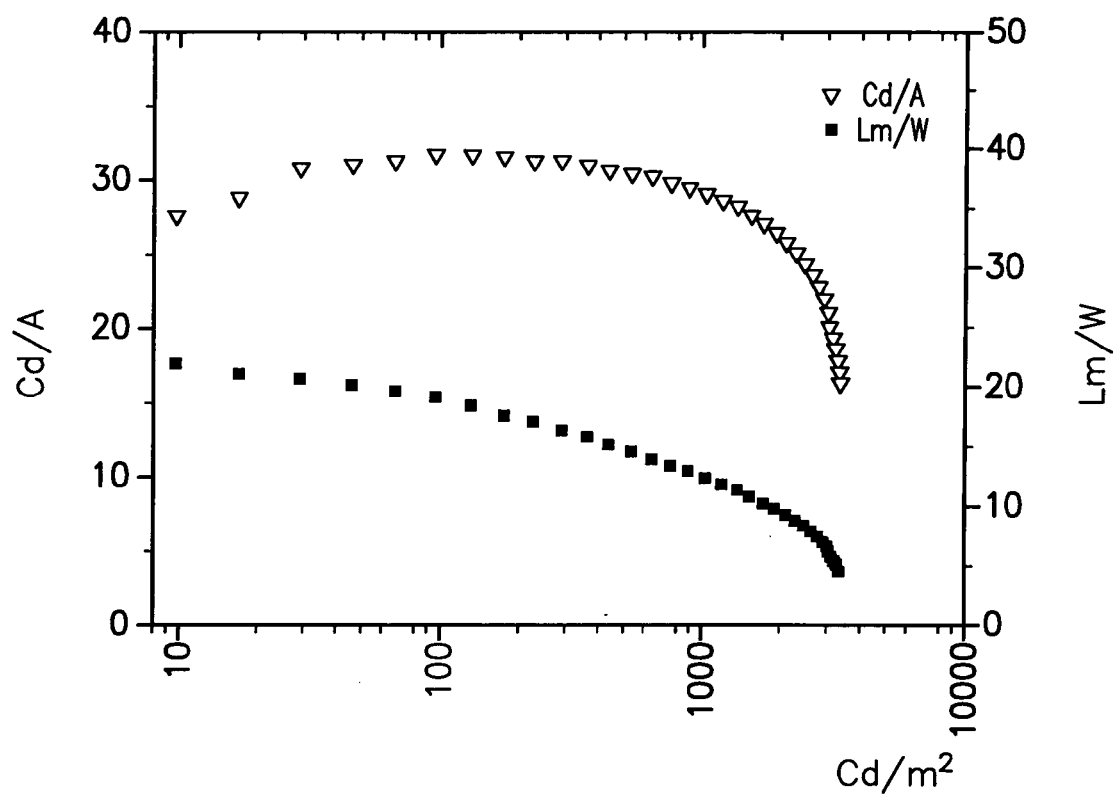
FIG. 11 shows the current efficiency and power efficiency versus luminance obtained for the device with Formula IX.

Plots of the current efficiency and power efficiency versus luminance obtained for the device with Formula IX are depicted in FIG. 11.

The invention claimed is:
1. A multinuclear complex of Formula (I):

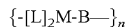

wherein
L, being the same or different at each occurrence, is a bidentate ligand, represented by:

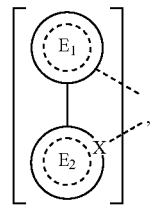

wherein $E_1$ represents an aromatic or heteroaromatic ring, optionally condensed with additional aromatic moieties or non aromatic cycles, said ring optionally having one or more substituents and coordinating to metal M via a $sp^2$ hybridized carbon, optionally forming a condensed structure with a ring comprising $E_2$; and wherein E₂ represents an aromatic or hetero-aromatic ring, optionally condensed with additional aromatic moieties or non aromatic cycles, said ring optionally having one or more substituents and coordinating to metal M via an atom X selected from groups IVa, Va or VIa of the periodic system;

M is Ir;

B is a 2-connecting short metal bridging ligand bound to said at least two metal atoms, wherein the metal bridging ligand comprises coordinating atoms independently selected from the group of nitrogen, phosphorous, carbon, oxygen, sulfur and selenium in 1,2 or 1,3 mutual position.(1,2-μ or 1,3-μ bonding mode);

and n is an integer larger than 1.

2. The multinuclear complex according to claim 1, wherein each B, being the same or different, is a short-bridging pseudo-halide ligand independently selected from the group consisting of:

CN— (cyano);
dicyanamide, tricyanomethanide;
NCX—, where X=O (iso-cyantes), or S (iso-thiocyanates), or Se (iso-selenocyanates);
$N_3$— (azides);
and
NO.

3. The multinuclear complex according to claim 2 wherein n=2 to 10.

4. The multinuclear complex according to claim 2 forming a macrocycle.

5. The multinuclear complex according to claim 2 wherein the bridging ligand is CN⁻.

6. The multinuclear complex according to claim 1 wherein coordinating atom X is carbon or nitrogen.

7. The multinuclear complex according to claim 6, wherein the complex has the following formula:

Formula (II)

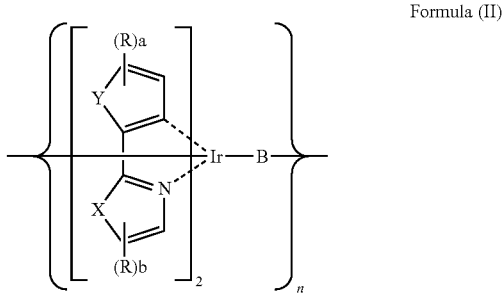

wherein:

X is selected from the group consisting of —CH=CH—, —CR=CH—, —CR=CR—, N—H, N—$R^1$, O, S, and Se;

Y is selected from the group consisting of —CH=CH—, —CR=CH—, —CR=CR—, N—H, N—$R^1$, O, S and Se;

R, being the same or different at each occurrence, is —F, —Cl, —Br, —NO₂, —CN, or a straight-chain or branched or cyclic alkyl or alkoxy group or dialkylamino group having from 1 to 20 carbon atoms, each of which one or more nonadjacent —CH₂— groups may be replaced by —O—, —S—, —$NR^1$—, or —$CONR^2$—, and in each of which one or more hydrogen atoms may be replaced by F, —$COOR^3$, an aryl or heteroaryl group having from 4 to 14 carbon atoms which may be substituted by one or more non aromatic radicals, wherein a plurality of R, either on the same ring or on two different rings, may in turn together form a mono- or polycyclic ring, optionally aromatic; wherein $R^1$, $R^2$, and $R^3$, being the same or different at each occurrence, are H or an aliphatic or aromatic hydrocarbon radical having from 1 to 20 carbon atoms;

a is an integer from 0 to 4; and
b is an integer from 0 to 4.

8. The multinuclear complex according to claim 6, wherein the complex has the following formula:

Formula (III)

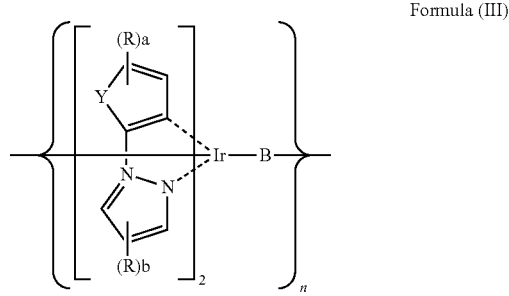

wherein:

Y is selected from the group consisting of —CH=CH—, —CR=CH—, —CR=CR—, N—H, N—$R^1$, O, S, and Se;

R, being the same or different at each occurrence, is —Cl, —Br, —NO₂, —CN, or a straight-chain or branched or cyclic alkyl or alkoxy group or dialkylamino group having from 1 to 20 carbon atoms, each of which one or more nonadjacent —CH₂— groups may be replaced by —O—, —S—, —$NR^1$—, or —$CONR^2$—, and in each of which one or more hydrogen atoms may be replaced by F, —$COOR^3$, an aryl or heteroaryl group having from 4 to 14 carbon atoms which may be substituted by one or more non aromatic radicals, wherein a plurality of R, either on the same ring or on two different rings, may in turn together form a mono- or polycyclic ring, optionally aromatic; wherein $R^1$, $R^2$, and $R^3$, being the same or different at each occurrence, are H or an aliphatic or aromatic hydrocarbon radical having from 1 to 20 carbon atoms;

a is an integer from 0 to 4;
b is an integer from 0 to 3; and
n is an integer larger than 1.

9. The multinuclear complex according to claim 6, wherein the complex has the following formula:

Formula (IV)

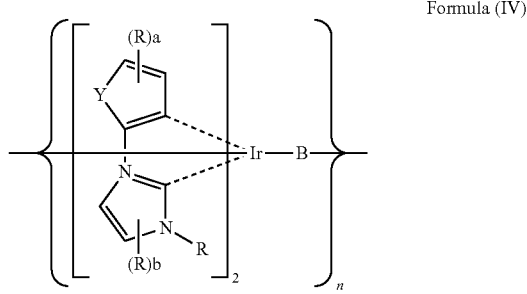

wherein:

Y is selected from the group consisting of —CH=CH—, —CR=CR—, —CR=CR—, N—H, N—$R^1$, O, S, and Se;

R, being the same or different at each occurrence, is —F, —Cl, —Br, —NO₂, —CN, or a straight-chain or branched or cyclic alkyl or alkoxy group or dialkylamino group having from 1 to 20 carbon atoms, each of which one or more nonadjacent —CH$_2$— groups may be replaced by —O—, —S—, —NR$^1$—, or —CONR$^2$—, and in each of which one or more hydrogen atoms may be replaced by F, —COOR$^3$, an aryl or heteroaryl group having from 4 to 14 carbon atoms which may be substituted by one or more non aromatic radicals, wherein a plurality of R, either on the same ring or on two different rings, may in turn together form a mono- or polycyclic ring, optionally aromatic; wherein R$^1$, R$^2$, and R$^3$, being the same or different at each occurrence, are H or an aliphatic or aromatic hydrocarbon radical having from 1 to 20 carbon atoms;

a is an integer from 0 to 4;

b is an integer from 0 to 2; and n is an integer larger than 1.

10. The multinuclear complex according to claim 6, wherein the complex has the following formula:

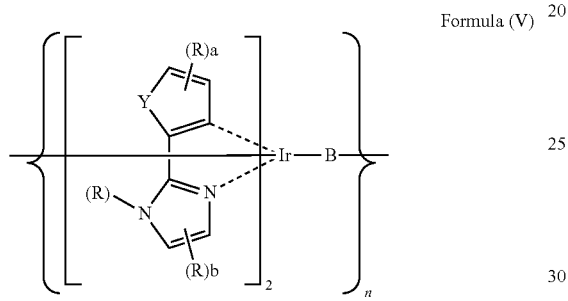

Formula (V)

wherein:

Y is selected from the group consisting of —CH=CH—, —CR=CH—, —CR=CR—, N—H, N—R$^1$, O, S, and Se;

R, being the same or different at each occurrence, is —F, —Cl, —Br, —NO$_2$, —CN, or a straight-chain or branched or cyclic alkyl or alkoxy group or dialkylamino group having from 1 to 20 carbon atoms, each of which one or more nonadjacent —CH$_2$— groups may be replaced by —O—, —S—, —NR$^1$—, or —CONR$^2$—, and in each of which one or more hydrogen atoms may be replaced by F, —COOR$^3$, an aryl or heteroaryl group having from 4 to 14 carbon atoms which may be substituted by one or more non aromatic radicals, wherein a plurality of R, either on the same ring or on two different rings, may in turn together form a mono- or polycyclic ring, optionally aromatic; wherein R$^1$, R$^2$, and R$^3$, being the same or different at each occurrence, are H or an aliphatic or aromatic hydrocarbon radical having from 1 to 20 carbon atoms;

a is an integer from 0 to 4;

h is an integer from 0 to 2; and n is an integer larger than 1.

11. The multinuclear complex according to claim 6, wherein the complex has a formula selected from the group consisting of:

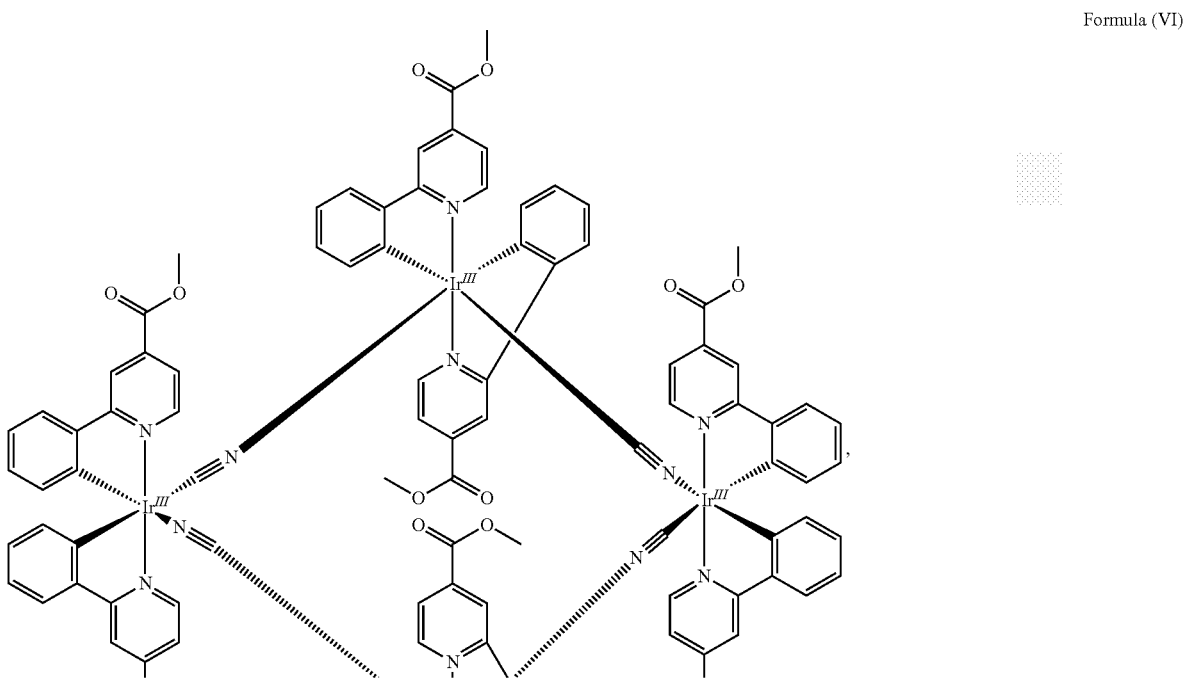

Formula (VI)

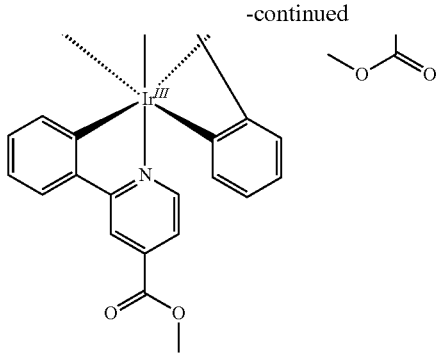
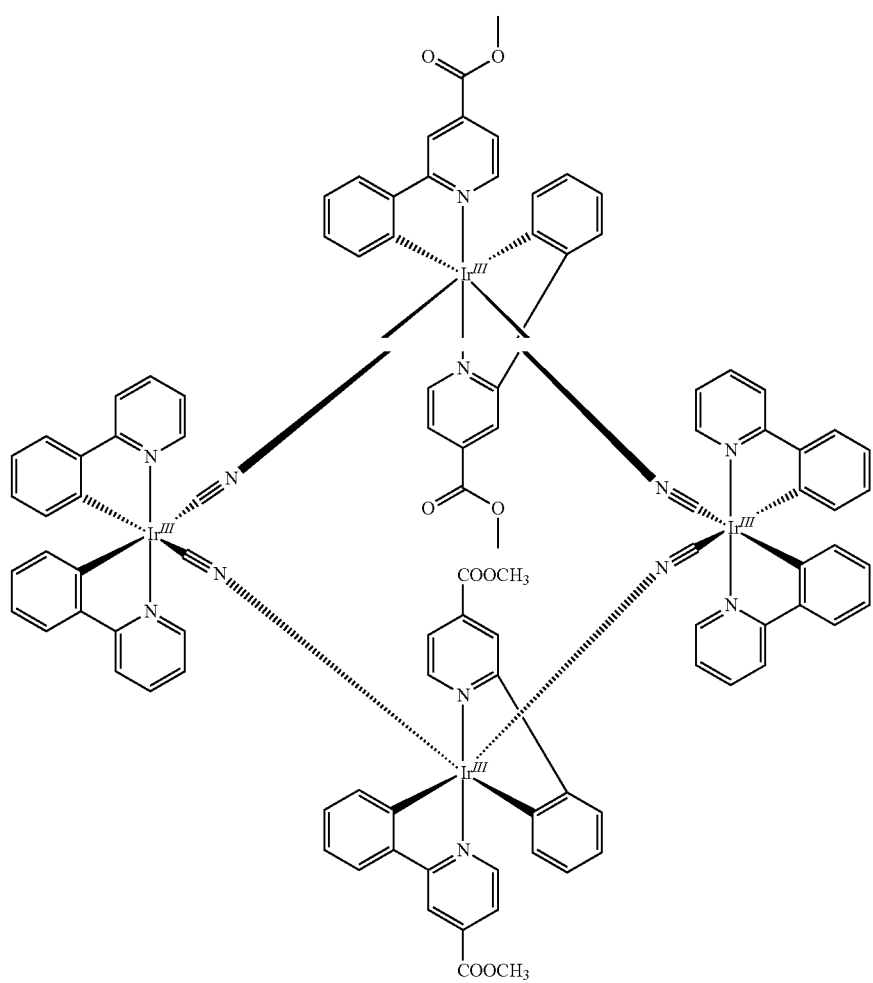
Formula (VII)
Formula (VIII)

-continued
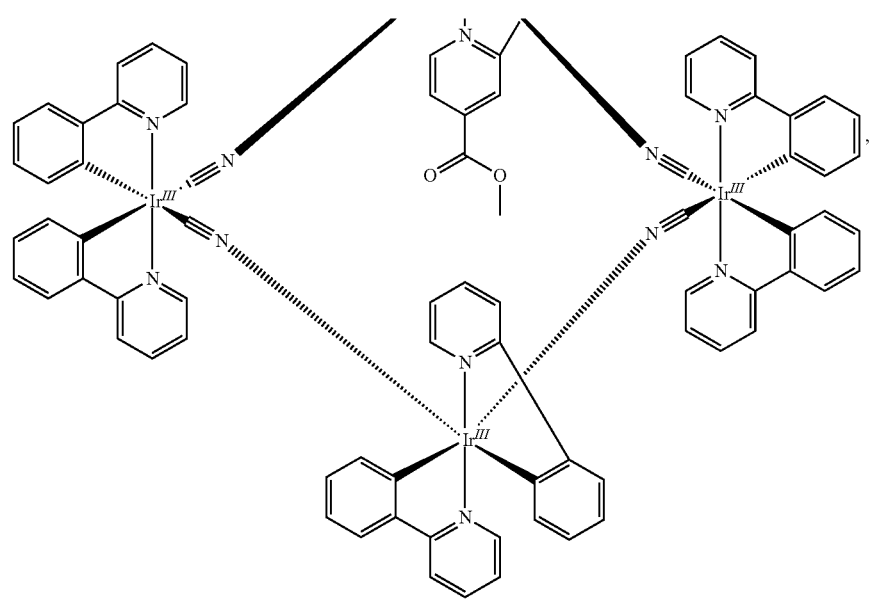
Formula (IX)
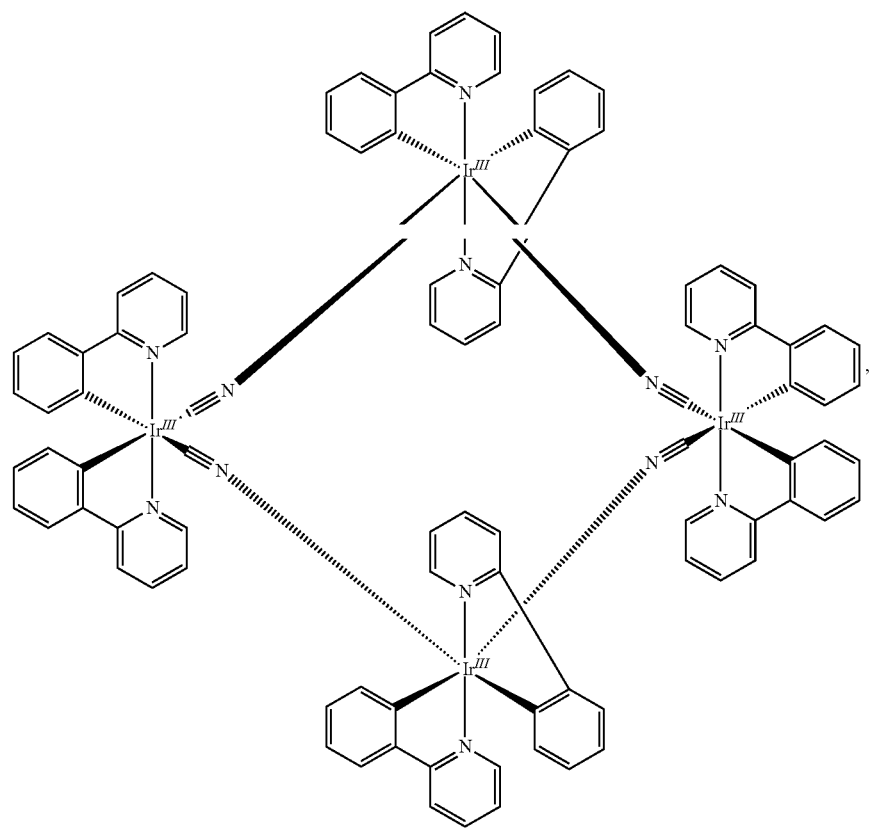

-continued
Formula (X)
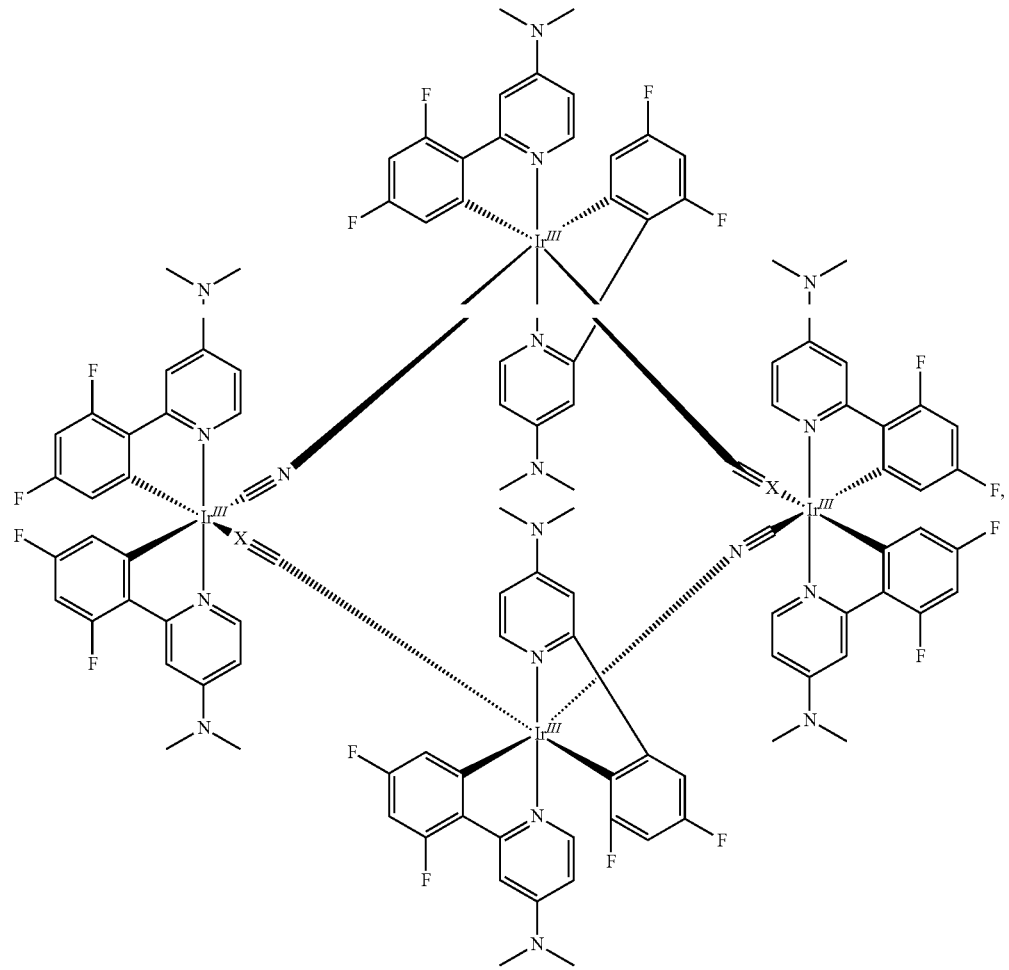
Formula (XI)
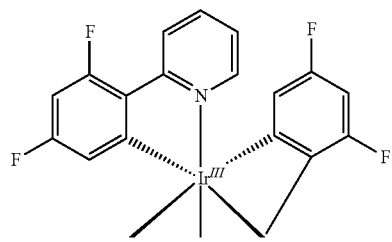

-continued
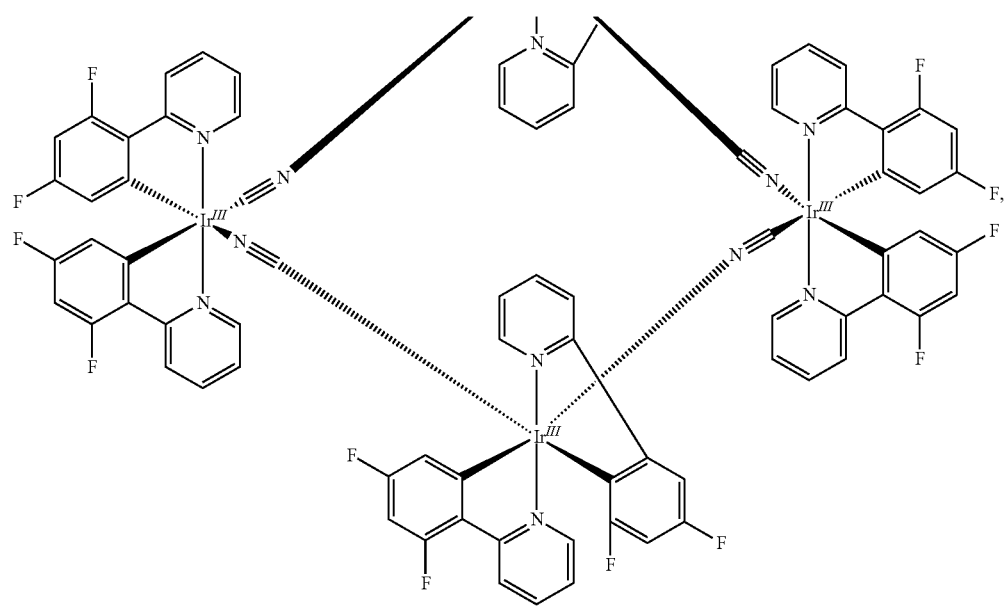
 Formula (XII)
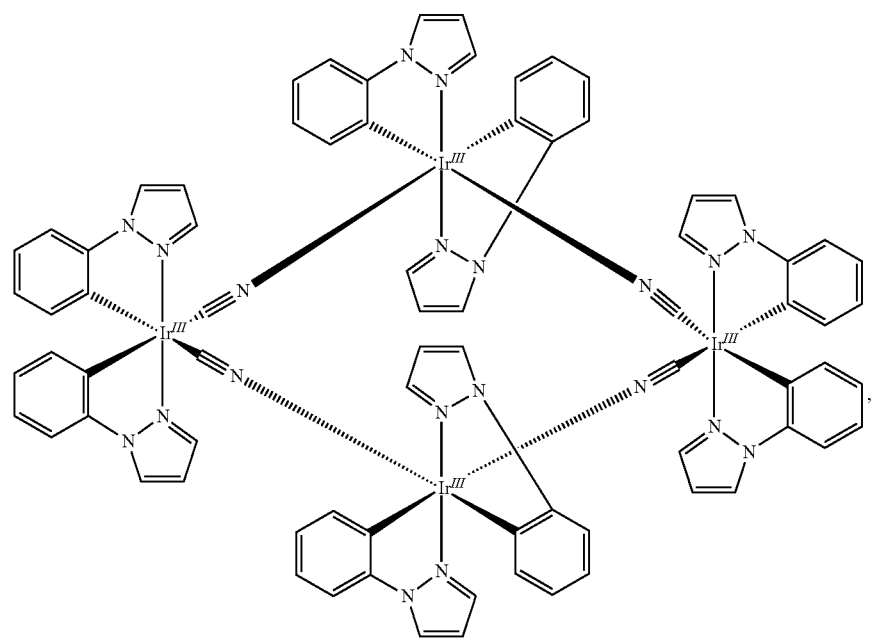

-continued
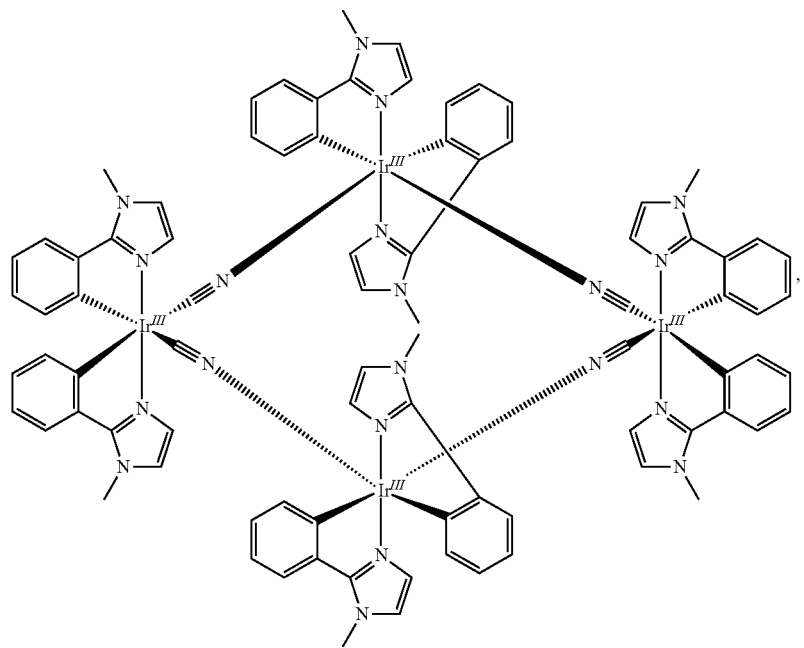
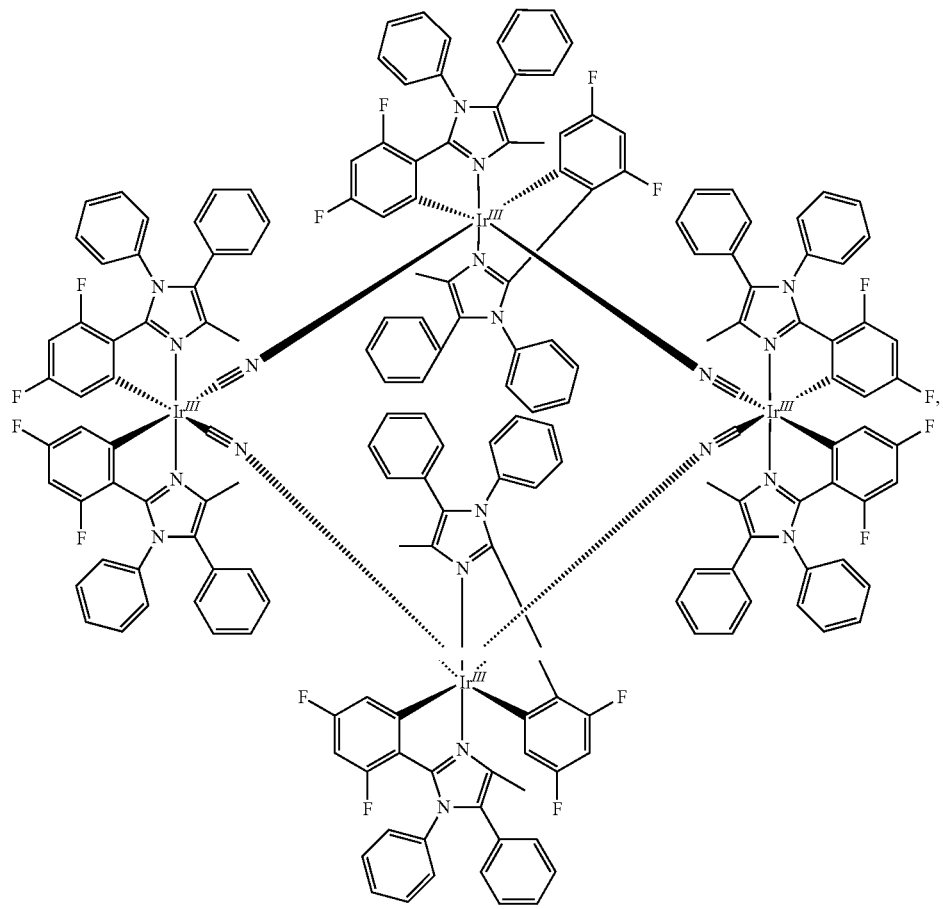

-continued
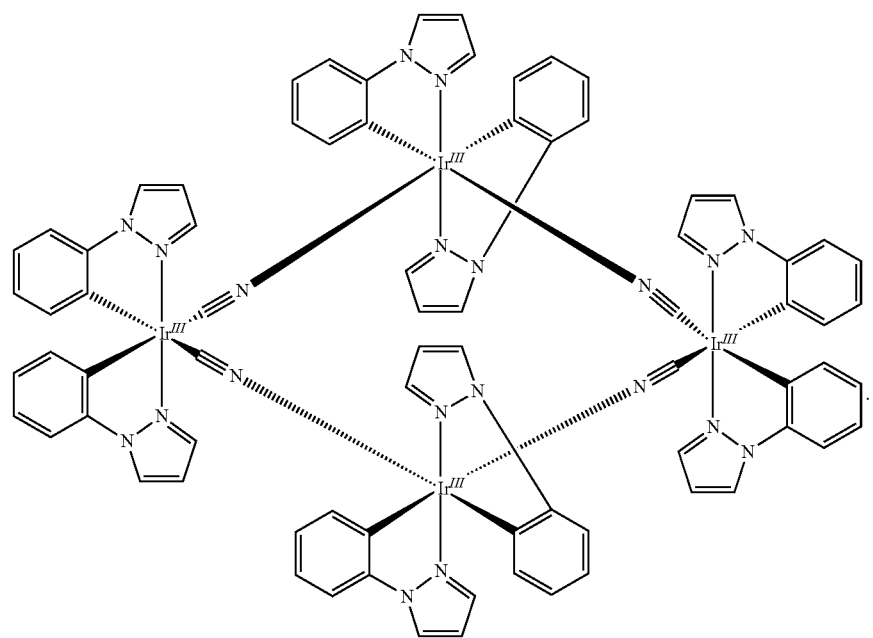
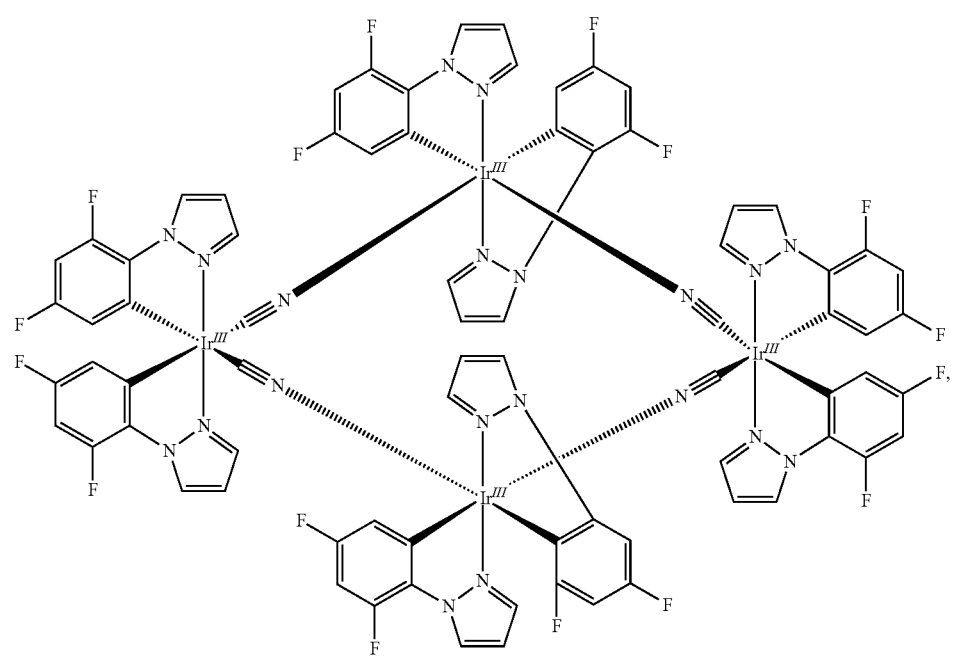

-continued
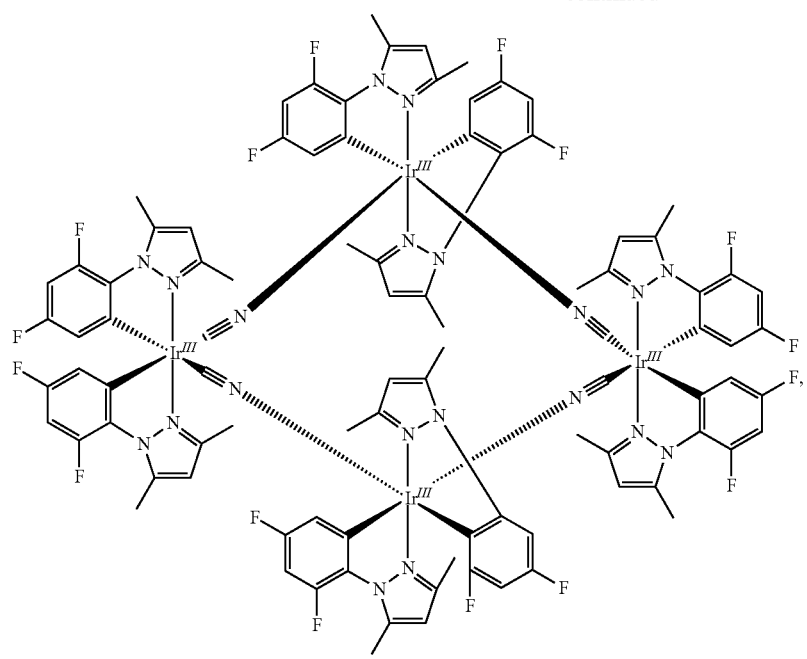
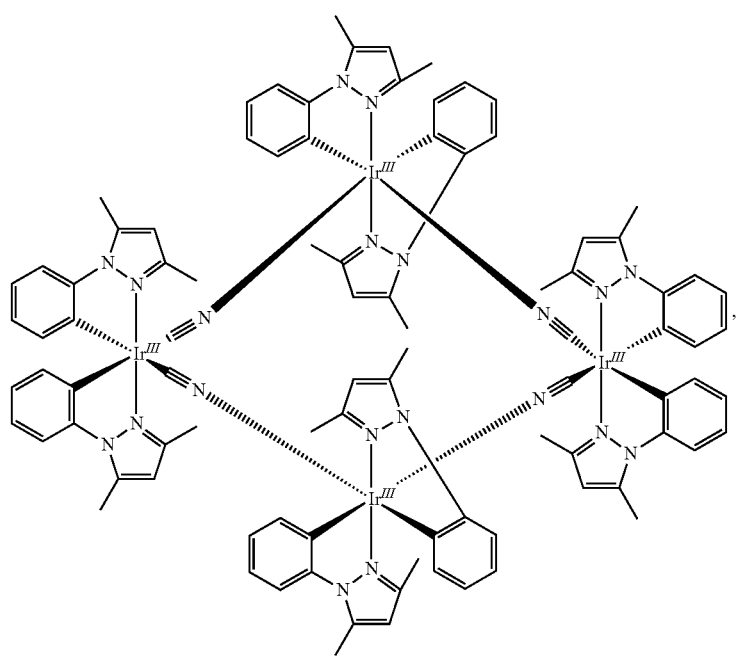
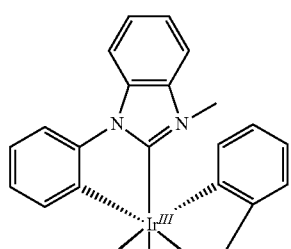

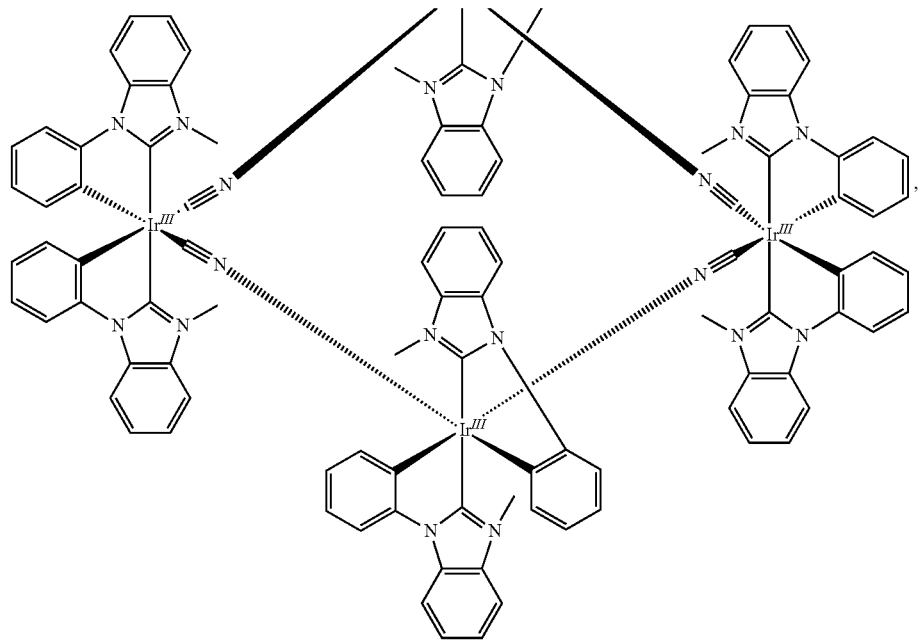
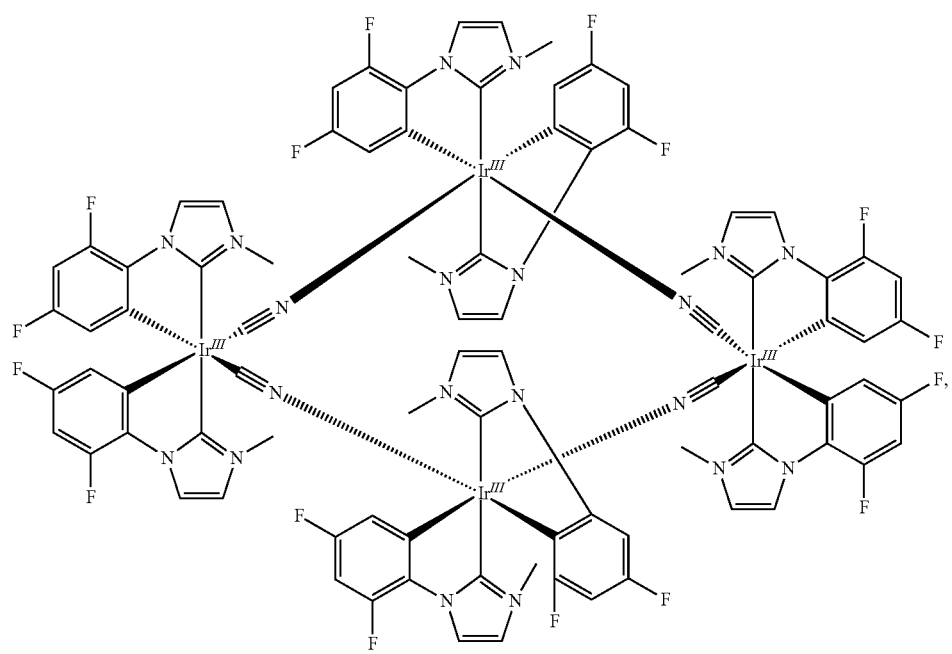
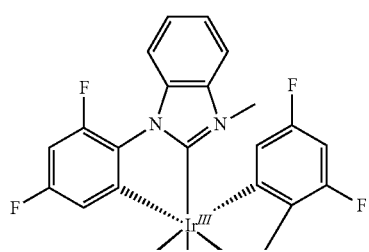

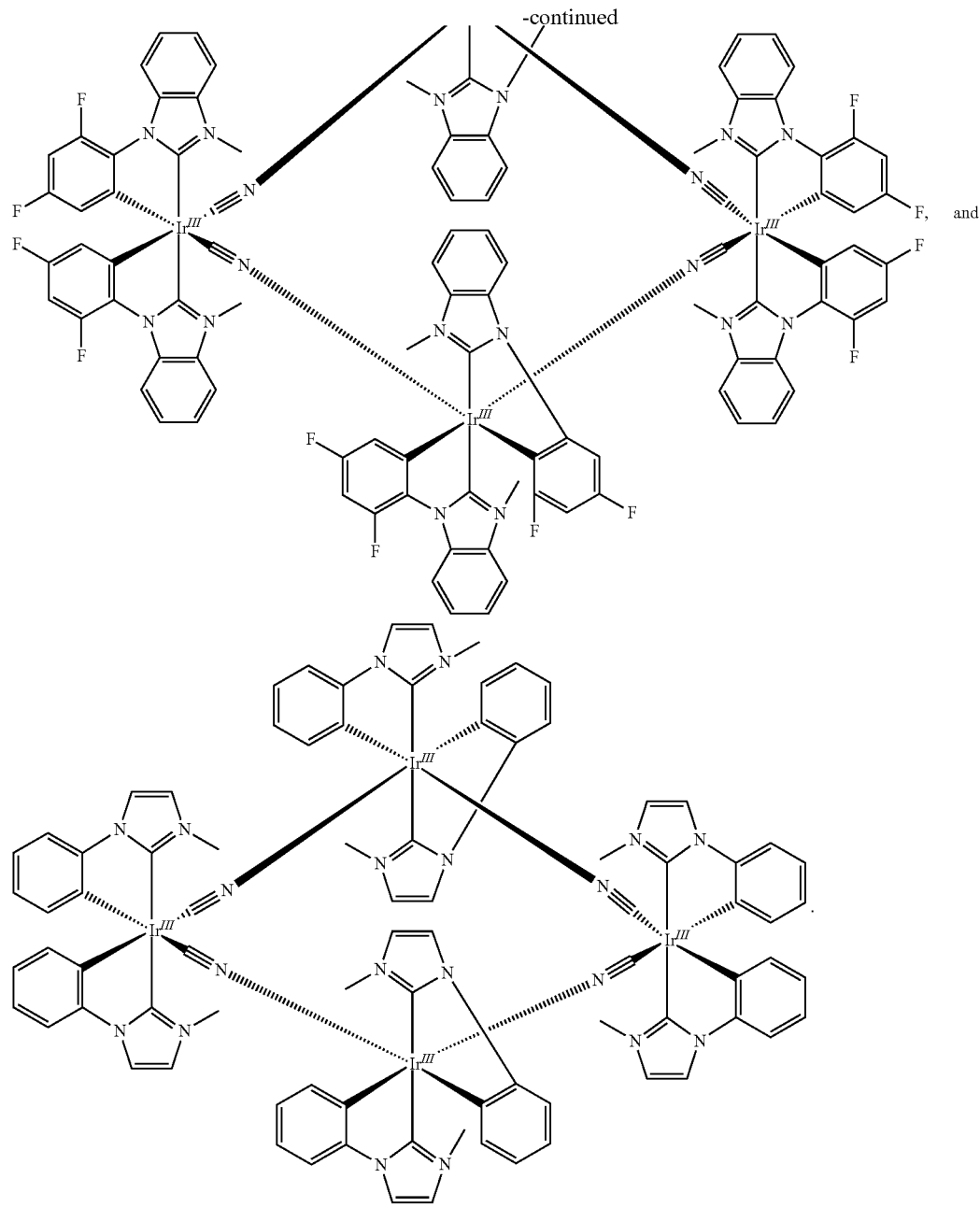
12. The multinuclear complex according to claim 6, wherein the complex has the following formula selected from the group consisting of:
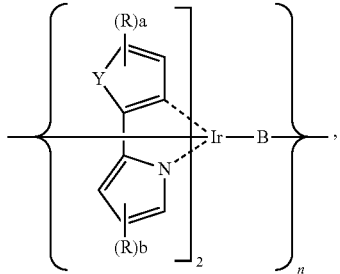
Formula (II)
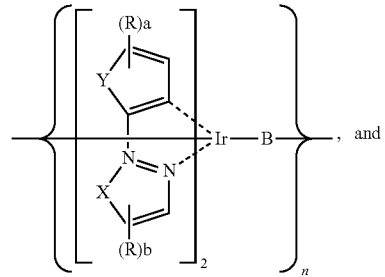
Formula (III)

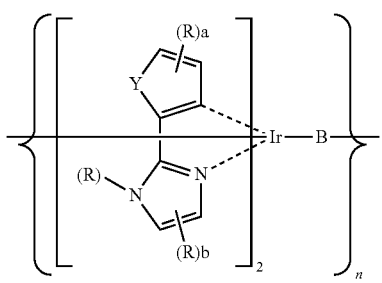

Formula (V)

wherein:
X is a group selected from the group consisting of —CH=CH—, —CR=CH—, and S;
Y is a group selected from the group consisting of —CR=CH—, —CR=CH—, and S;
R, being the same or different at each occurrence, is —F, —Cl, —Br, —NO$_2$, —CN, or a straight-chain or branched or cyclic alkyl or alkoxy group or dialkylamino group having from 1 to 20 carbon atoms, each of which one or more nonadjacent —CH$_2$— groups may be replaced by —O—, —S—, or —CONR$^2$—, and in each of which one or more hydrogen atoms may be replaced by F, —COOR$^3$, an aryl or heteroaryl group having from 4 to 14 carbon atoms which may be substituted by one or more non aromatic radicals, wherein a plurality of R, either on the same ring or on two different rings, may in turn together form a mono- or polycyclic ring, optionally aromatic; wherein R$^1$, R$^2$, and R$^3$, being the same or different at each occurrence, are H or an aliphatic or aromatic hydrocarbon radical having from 1 to 20 carbon atoms;
a is an integer from 0 to 4;
b is an integer from 0 to 4 for formula (II), an integer from 0 to 3 for formula (III), or an integer from 0 to 2 for formula (IV); and
n is an integer larger than 1.

13. The multinuclear complex according to claim 12, wherein X or Y is —CH=CH—.

14. The multinuclear complex according to claim 1 wherein n=2 to 10.

15. The multinuclear complex according to claim 14 wherein n=4.

16. The multinuclear complex according to claim 1 forming a macrocycle.

17. The multinuclear complex according to claim 1 wherein the bridging ligand is CN$^-$.

18. An organic light emitting device comprising an emissive layer, wherein said emissive layer comprises the multinuclear complex according to claim 1 as light emitting material, and optionally a host material.

19. A display device comprising the organic light emitting device according to claim 18.

* * * * *